US009652840B1

(12) United States Patent
Shriver et al.

(10) Patent No.: US 9,652,840 B1
(45) Date of Patent: May 16, 2017

(54) SYSTEM AND METHOD FOR REMOTE NITROGEN MONITORING AND PRESCRIPTION

(71) Applicant: AgriSight, Inc., Ann Arbor, MI (US)

(72) Inventors: John Shriver, Ann Arbor, MI (US); Rishi Prasad, Ann Arbor, MI (US); Michael Asher, Ann Arbor, MI (US); Tracy Blackmer, Ann Arbor, MI (US)

(73) Assignee: AgriSight, Inc., Ann Arbor, MI (US)

( * ) Notice: Subject to any disclaimer, the term of this patent is extended or adjusted under 35 U.S.C. 154(b) by 0 days.

(21) Appl. No.: 15/345,027

(22) Filed: Nov. 7, 2016

Related U.S. Application Data

(63) Continuation-in-part of application No. 14/929,055, filed on Oct. 30, 2015, and a continuation-in-part of application No. 15/012,762, filed on Feb. 1, 2016, and a continuation-in-part of application No. 15/012,749, filed on Feb. 1, 2016.
(Continued)

(51) Int. Cl.
| | |
|---|---|
| *G06K 9/00* | (2006.01) |
| *G06T 7/00* | (2017.01) |
| *G05B 15/02* | (2006.01) |
| *G01N 33/00* | (2006.01) |
| *G01N 33/02* | (2006.01) |
| *G06K 9/62* | (2006.01) |
| *G06K 9/46* | (2006.01) |

(Continued)

(52) U.S. Cl.
CPC ....... *G06T 7/0004* (2013.01); *G01N 33/0036* (2013.01); *G01N 33/025* (2013.01); *G05B 15/02* (2013.01); *G06K 9/4661* (2013.01); *G06K 9/6215* (2013.01); *G06K 9/6267* (2013.01); *G06K 9/66* (2013.01); *G06T 2207/30188* (2013.01); *G06T 2207/30192* (2013.01)

(58) Field of Classification Search
USPC ....... 382/100, 103, 106, 108, 155, 162, 168, 382/173, 187, 199, 206, 220, 232, 254, 382/274, 276, 286–291, 305, 312, 110; 435/252.2, 120; 111/118; 47/1.01
See application file for complete search history.

(56) References Cited

U.S. PATENT DOCUMENTS

| | | | |
|---|---|---|---|
| 4,570,378 A | * | 2/1986 | Wendt ................ A01G 13/0262 111/118 |
| 5,497,419 A | | 3/1996 | Hill |

(Continued)

FOREIGN PATENT DOCUMENTS

WO    2014120887 A1    8/2014

OTHER PUBLICATIONS

At Your Fingertips. American Vegetable Grower, vol. 61, No. 7, Jul. 2013.
(Continued)

*Primary Examiner* — Seyed Azarian
(74) *Attorney, Agent, or Firm* — Jeffrey Schox; Diana Lin

(57) ABSTRACT

A method and system for managing nitrogen applied by nitrogen application equipment to a geographic region includes determining a growth stage for the geographic region using a crop module, and determining a nitrogen change for the geographic region based on the growth stage using a nitrogen change module, which can additionally or alternatively include determining an amount of nitrogen initially available for a geographic region.

15 Claims, 12 Drawing Sheets

Related U.S. Application Data

(60) Provisional application No. 62/252,102, filed on Nov. 6, 2015, provisional application No. 62/072,911, filed on Oct. 30, 2014, provisional application No. 62/109,888, filed on Jan. 30, 2015, provisional application No. 62/130,314, filed on Mar. 9, 2015, provisional application No. 62/109,842, filed on Jan. 30, 2015, provisional application No. 62/154,936, filed on Apr. 30, 2015.

(51) Int. Cl.
*G06K 9/66* (2006.01)
*C12P 17/14* (2006.01)

(56) References Cited

U.S. PATENT DOCUMENTS

| | | | |
|---|---|---|---|
| 5,606,821 A * | 3/1997 | Sadjadi | A01M 7/0089 47/1.01 R |
| 5,699,244 A | 12/1997 | Clark et al. | |
| 5,751,576 A | 5/1998 | Monson | |
| 5,878,371 A | 3/1999 | Hale et al. | |
| 5,884,224 A | 3/1999 | McNabb et al. | |
| 5,938,709 A | 8/1999 | Hale et al. | |
| 5,978,723 A | 11/1999 | Hale et al. | |
| 6,141,614 A | 10/2000 | Janzen et al. | |
| 6,525,276 B1 | 2/2003 | Vellidus et al. | |
| 6,601,341 B2 | 8/2003 | Raun et al. | |
| 6,606,542 B2 | 8/2003 | Hauwiller et al. | |
| 6,751,515 B2 | 6/2004 | Moore | |
| 7,031,927 B1 | 4/2006 | Beck et al. | |
| 7,058,197 B1 | 6/2006 | McGuire et al. | |
| 7,068,816 B1 | 6/2006 | Knoblauch et al. | |
| 7,103,451 B2 | 9/2006 | Seal et al. | |
| 7,171,912 B2 | 2/2007 | Fraisse et al. | |
| 7,974,849 B1 | 7/2011 | Begole et al. | |
| 8,671,006 B2 * | 3/2014 | Zyskowski | G06Q 10/06 435/252.2 |
| 8,731,836 B2 | 5/2014 | Lindores et al. | |
| 9,026,139 B2 | 5/2015 | Sen | |
| 9,058,633 B2 | 6/2015 | Lindores et al. | |
| 9,113,590 B2 | 8/2015 | Johnson | |
| 9,117,140 B2 * | 8/2015 | Purcell | G01N 21/25 |
| 9,131,644 B2 | 9/2015 | Osborne | |
| 2001/0036295 A1 | 11/2001 | Hendrickson et al. | |
| 2002/0091458 A1 | 7/2002 | Moore | |
| 2003/0028321 A1 | 2/2003 | Upadhyaya et al. | |
| 2004/0077347 A1 | 4/2004 | Lauber et al. | |
| 2004/0194442 A1 | 10/2004 | Maertens | |
| 2005/0108100 A1 | 5/2005 | Veen et al. | |
| 2005/0137803 A1 | 6/2005 | Kleemola et al. | |
| 2006/0017551 A1 | 1/2006 | Neher et al. | |
| 2006/0106539 A1 | 5/2006 | Choate et al. | |
| 2007/0038338 A1 | 2/2007 | Larschan et al. | |
| 2007/0065857 A1 | 3/2007 | Glaser et al. | |
| 2007/0150209 A1 | 6/2007 | McPherson et al. | |
| 2008/0157990 A1 | 7/2008 | Belzer et al. | |
| 2008/0195268 A1 | 8/2008 | Sapilewski et al. | |
| 2008/0304711 A1 * | 12/2008 | Scharf | A01C 21/007 382/110 |
| 2009/0164054 A1 | 6/2009 | Peterson et al. | |
| 2009/0216594 A1 | 8/2009 | Verhey et al. | |
| 2010/0069035 A1 | 3/2010 | Johnson | |
| 2010/0306012 A1 | 12/2010 | Zyskowski et al. | |
| 2011/0270723 A1 | 11/2011 | O'Neil | |
| 2011/0270724 A1 | 11/2011 | Waggoner | |
| 2011/0290873 A1 | 12/2011 | Nishiguchi et al. | |
| 2012/0005105 A1 | 1/2012 | Beier et al. | |
| 2012/0072922 A1 | 3/2012 | O'Neil | |
| 2012/0101634 A1 | 4/2012 | Lindores | |
| 2012/0101784 A1 | 4/2012 | Lindores et al. | |
| 2012/0123817 A1 | 5/2012 | Hohenberger et al. | |
| 2012/0237083 A1 | 9/2012 | Lange et al. | |
| 2012/0280797 A1 | 11/2012 | Meyers | |
| 2013/0144827 A1 | 6/2013 | Trevino | |
| 2013/0185104 A1 | 7/2013 | Klavins | |
| 2013/0226607 A1 | 8/2013 | Woody et al. | |
| 2013/0275187 A1 | 10/2013 | Patel | |
| 2014/0012732 A1 | 1/2014 | Lindores | |
| 2014/0058881 A1 | 2/2014 | Rosenbaum | |
| 2014/0128105 A1 | 5/2014 | Su et al. | |
| 2014/0205154 A1 | 7/2014 | De Souza et al. | |
| 2014/0278645 A1 | 9/2014 | Davidson et al. | |
| 2015/0025926 A1 | 1/2015 | Green et al. | |
| 2015/0040473 A1 | 2/2015 | Lankford | |
| 2015/0070188 A1 | 3/2015 | Aramburu | |
| 2015/0163992 A1 | 6/2015 | Anderson | |
| 2015/0234767 A1 | 8/2015 | Tatge et al. | |
| 2015/0242970 A1 | 8/2015 | Avey et al. | |
| 2015/0254800 A1 | 9/2015 | Johnson et al. | |
| 2015/0272105 A1 | 10/2015 | Peterson | |
| 2015/0278640 A1 | 10/2015 | Johnson et al. | |
| 2015/0278838 A1 | 10/2015 | Rasa et al. | |
| 2015/0278966 A1 | 10/2015 | Johnson | |
| 2015/0302305 A1 | 10/2015 | Rupp et al. | |
| 2016/0019560 A1 | 1/2016 | Benkert et al. | |
| 2016/0026940 A1 | 1/2016 | Johnson | |
| 2016/0078375 A1 | 3/2016 | Ethington et al. | |
| 2016/0078570 A1 | 3/2016 | Ethington et al. | |
| 2016/0112362 A1 | 4/2016 | Perazzo et al. | |
| 2016/0180473 A1 | 6/2016 | Groeneveld | |

OTHER PUBLICATIONS

Bennett, Jen, New Croup Scouting and Farm Management Apps Available. Corn and Soybean Digest, Jul. 3, 2013.
FarmLogs.com Website. FarmLogs, Feb. 2013, Retrieved from Archive.org Feb. 10, 2016.
Friess, Steve, FarmLogs App Helps Farmers Collect and Retrieve Data. The New York Times, Jun. 24, 2015.
New Software Increases Productivity. American Fruit Grower, vol. 133, No. 7, Jul. 2013.
New UNL Extension App Helps Pesticide Applicators Keep Electronic Records. IANR News, May 20, 2013.
Stross, Randall, Letting the Cloud Watch Over the Farm. New York Times, Aug. 5, 2012.
Swoboda, Rod, Smart way to keep crop records. Wallaces Farmer, vol. 127, No. 3, Feb. 2002.
Virtual Fields: Farming Apps The Economist, Apr. 30, 2013.
Welte, Jonathan Tyler, A Farm Management Information System with Task-Specific, Collaborative Mobile Apps and Cloud Storage Services, Purdue University, May 2014.

* cited by examiner

SYSTEM AND METHOD FOR REMOTE NITROGEN MONITORING AND PRESCRIPTION

CROSS-REFERENCE TO RELATED APPLICATIONS

This application claims the benefit of U.S. Provisional Application No. 62/252,102 filed 6 Nov. 2015, which is incorporated in its entirety by this reference.

This application is a continuation-in-part of U.S. application Ser. No. 14/929,055 filed 30 Oct. 2015, which claims priority to U.S. Provisional Application No. 62/072,911 filed 30 Oct. 2014, U.S. application Ser. No. 15/012,762 filed 1 Feb. 2016, which claims priority to U.S. Provisional Application No. 62/109,888 filed on 30 Jan. 2015 and U.S. Provisional Application No. 62/130,314 filed on 9 Mar. 2015, and U.S. application Ser. No. 15/012,749 filed 1 Feb. 2016, which claims priority to U.S. Provisional Application No. 62/109,842 filed 30 Jan. 2015 and U.S. Provisional Application No. 62/154,936 filed 30 Apr. 2015, all of which are incorporated herein in their entireties by this reference.

TECHNICAL FIELD

This invention relates generally to the agricultural field, and more specifically to a new and useful nitrogen monitoring and prescription system and method in the agricultural field.

DESCRIPTION OF THE PREFERRED EMBODIMENTS

The following description of the preferred embodiments of the invention is not intended to limit the invention to these preferred embodiments, but rather to enable any person skilled in the art to make and use this invention.

1. Overview

Figure 1A:
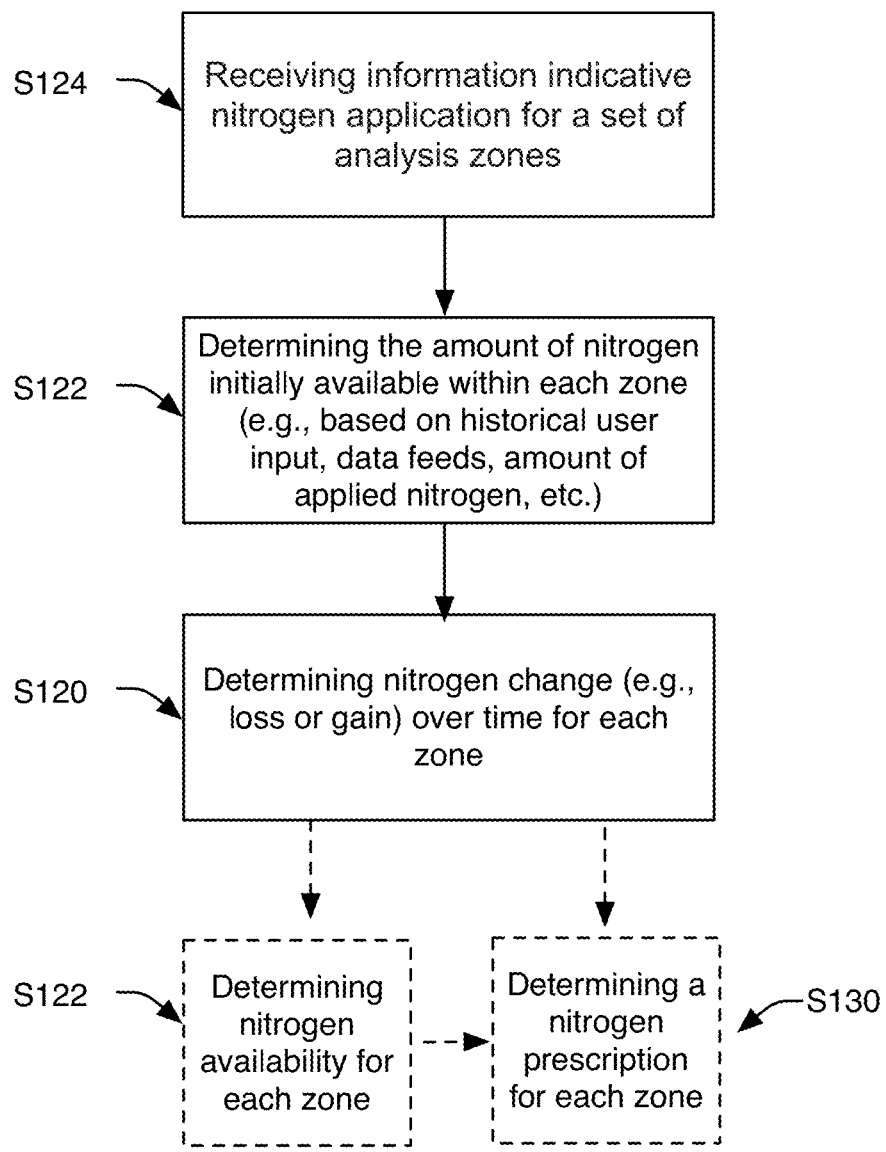
FIG. 1A-1B are flowchart diagrams of variations of the method of remote nitrogen monitoring.
Figure 1B:
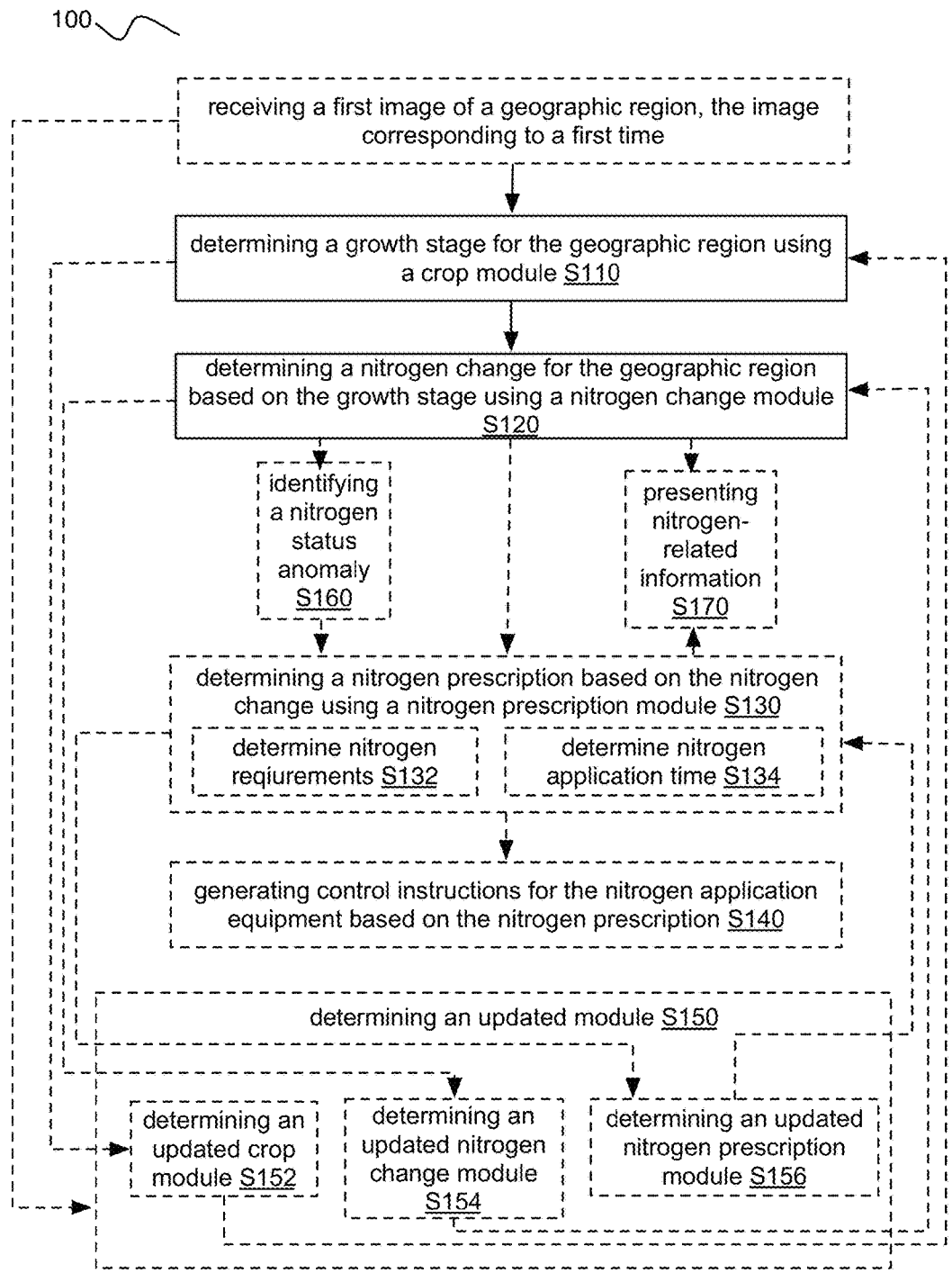
Figure 2:
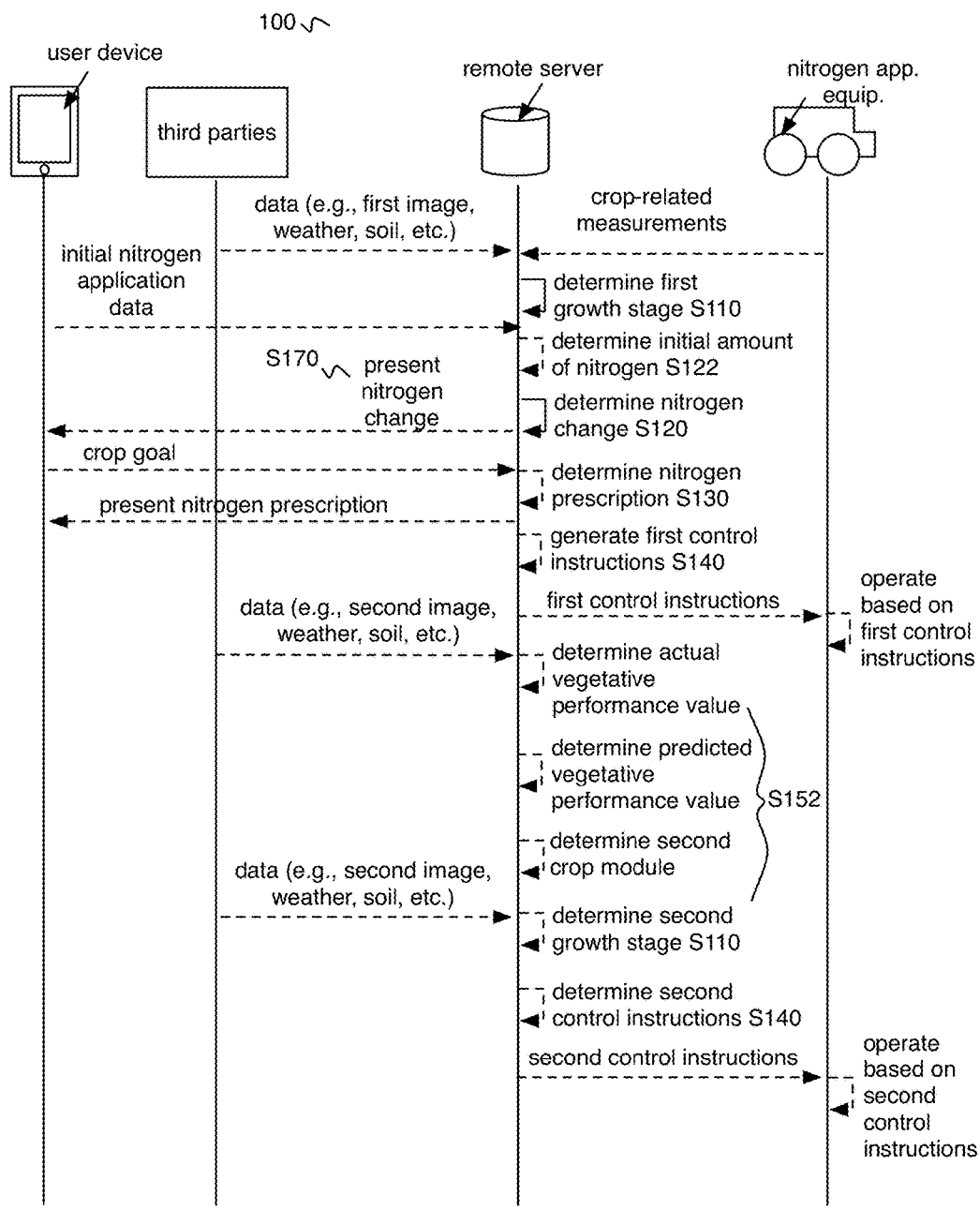
FIG. 2 is a flowchart diagram of a variation of the method of remote nitrogen monitoring.
Figure 3:
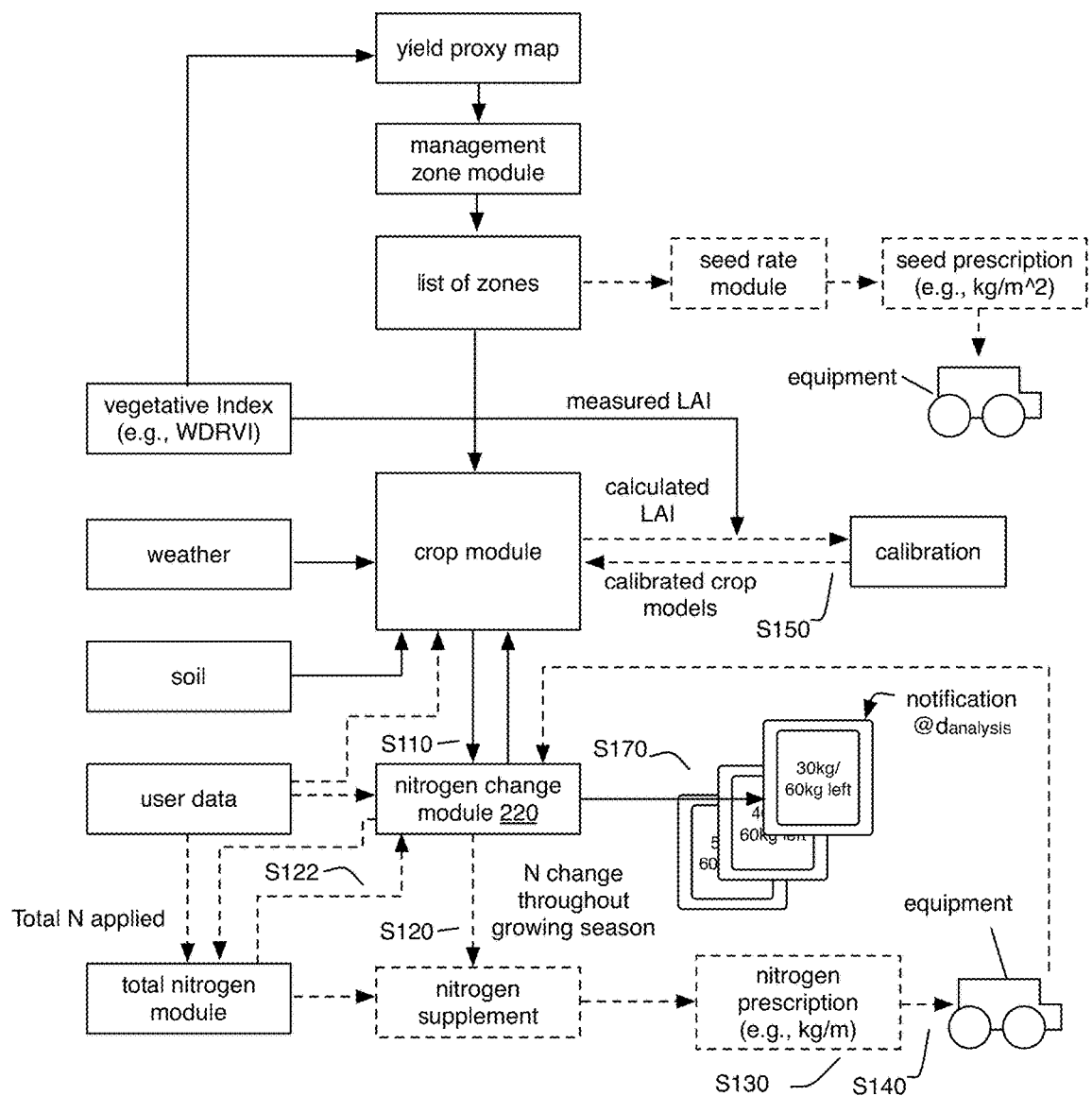
FIG. 3 is a schematic diagram of a variation of the method of remote nitrogen monitoring.
Figure 4:
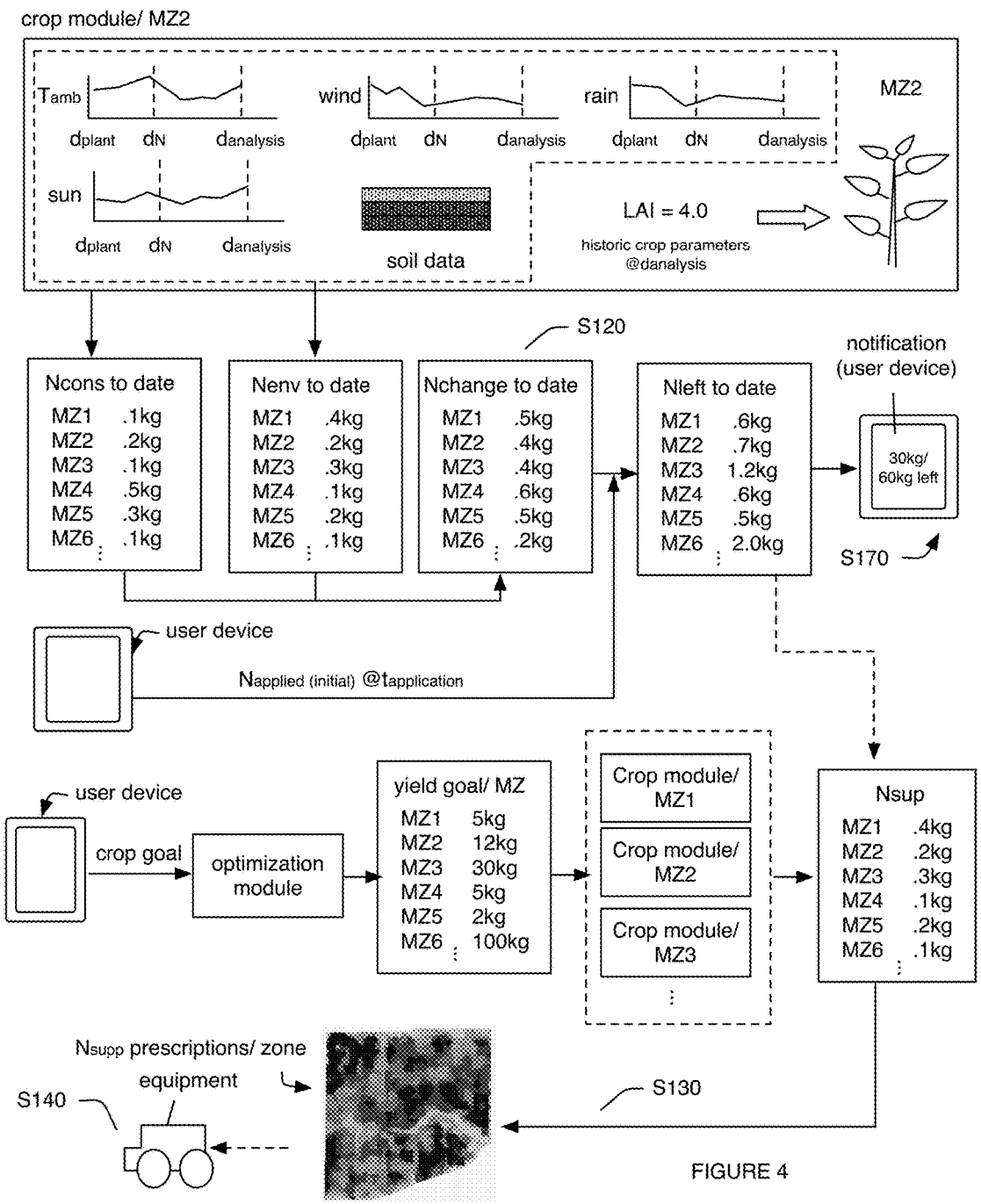
FIG. 4 is a schematic diagram of a variation of the method of remote nitrogen monitoring.
Figure 5:
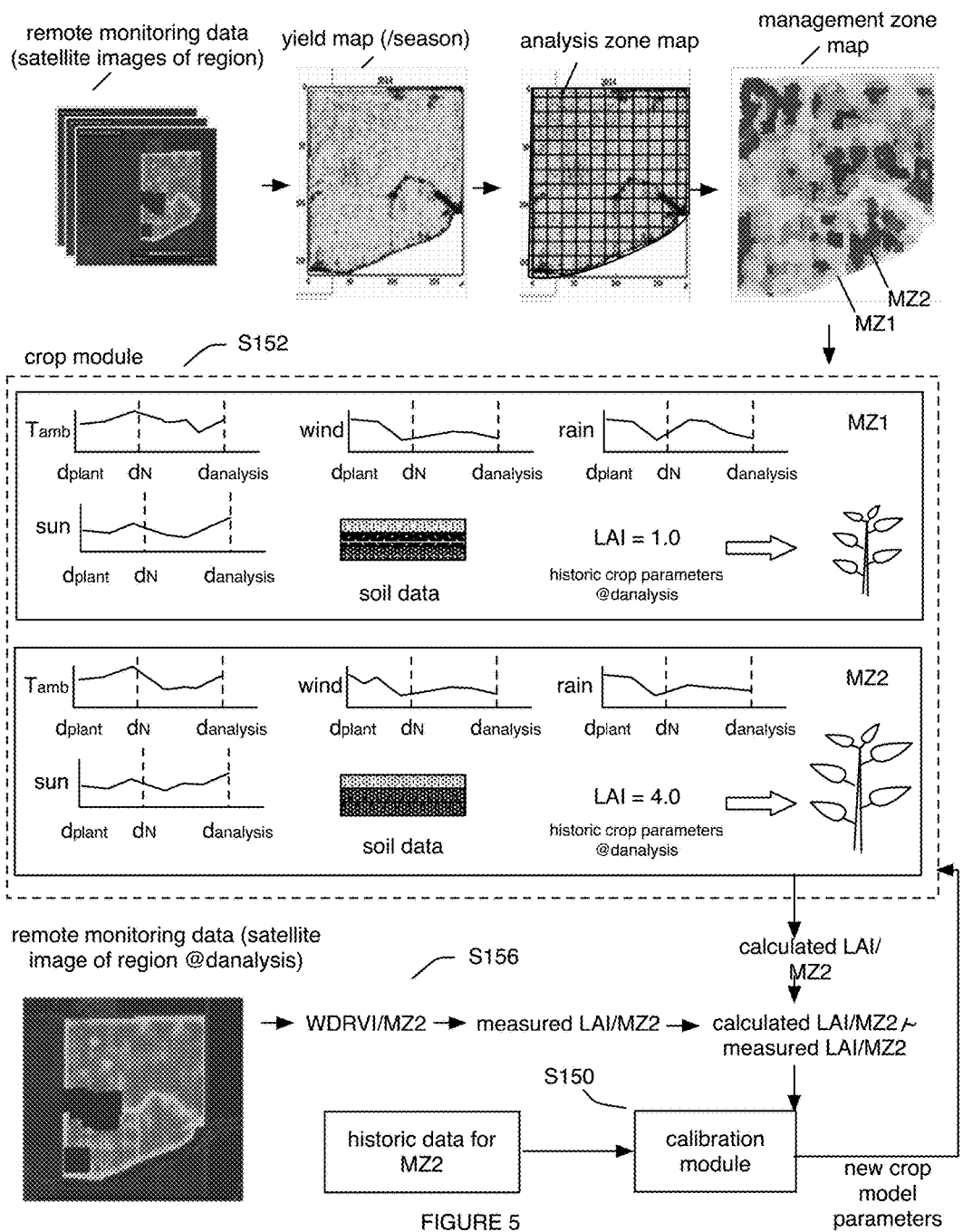
FIG. 5 is a schematic diagram of determining an updated module in a variation of the method of remote nitrogen monitoring.
Figure 6:
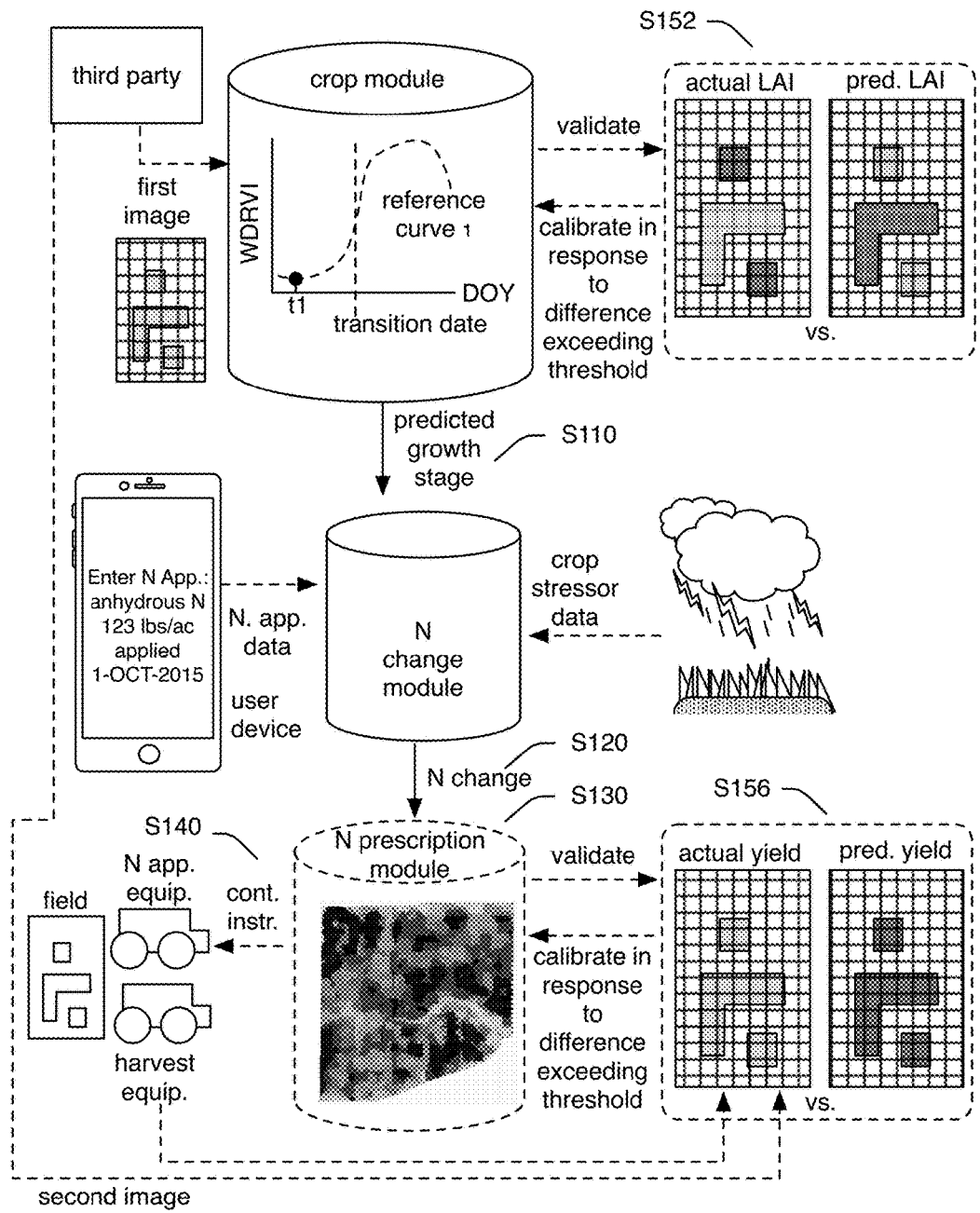
FIG. 6 is a schematic diagram of determining an updated module in a variation of the method of remote nitrogen monitoring.

As shown in FIGS. 1-3, a method 100 for managing nitrogen within a geographic region includes: determining a growth stage for the geographic region using a crop module S110; and determining a nitrogen change for the geographic region using a nitrogen change module S120. The method can additionally or alternatively include determining an amount of nitrogen initially available for a geographic region S122.

As shown in FIG. 1B, the method 100 can additionally or alternatively include determining a nitrogen prescription for the geographic region based on the nitrogen change using a nitrogen prescription module S130; generating control instructions for agricultural equipment based on the nitrogen prescription S140; determining an updated module S150 (e.g., an updated crop module S152, an updated nitrogen change module S152, an updated nitrogen prescription module S154, etc.); identifying a nitrogen status anomaly based on the nitrogen change S160; presenting nitrogen-related information to a user account S170; and/or reducing noise associated with remote imagery, module inputs (e.g., yield map), module outputs (e.g., nitrogen prescription), and/or any other suitable data. Reducing noise can include applying any one or more of: a bootstrap filter, registration noise reduction, particle filter, noise reduction heuristics, and/or any other processing operations.

The method 100 functions to determine the amount of nitrogen that is lost or gained from the geographic region (e.g., field), geographic sub-region (e.g., region of the field), and/or any suitable region over time. The method 100 can additionally or alternatively function to determine a nitrogen prescription (e.g., for initial fertilizer application, side dressing, etc.), which can be used for generating control instructions for agricultural equipment to apply nitrogen according to the nitrogen prescription. The nitrogen applied to the field or field sub-regions can function to augment the nitrogen remaining in the field to reach a target parameter, such as a target yield, growth stage distribution, or other parameter.

Any portion of the method 100 can be implemented with any combination of components of the system, and/or any suitable components.

2. Benefits

Nitrogen is an essential nutrient for crop growth and development. Therefore, there has been a long-felt need in the agricultural field to monitor the amount of nitrogen available to plants in the soil surrounding the plant. This need is in direct tension with the economic need to decrease treatment costs (e.g., fertilizer application costs) that arise from the low economic margins that can be gained from commodity products. However, nitrogen monitoring presents several challenges. First, due to the size of the fields, manual nitrogen measurements can be impractical and costly. Second, remote monitoring of nitrogen can be difficult given the lack of visual manifestation of the nitrogen on the field surface. Third, soil nitrogen can be highly mobile and dependent upon a plurality of factors (e.g., wind, rain, ambient temperature, microbial population, soil texture, crop growth stage, etc.), which can render computational modeling and/or prediction difficult. Fourth, groundtruth data for nitrogen-influenced effects can be rare and/or difficult to obtain.

In specific examples, the method 100 and/or system can confer several benefits over conventional methodologies used for determining nitrogen change, generating nitrogen prescriptions, and/or implementing nitrogen prescriptions.

Figure 9A:
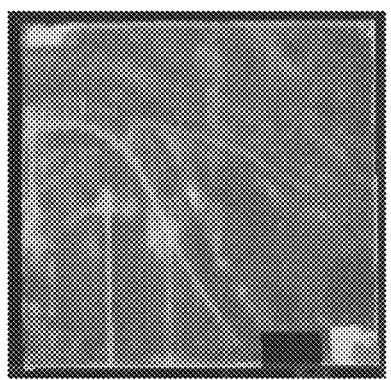
FIGS. 9A and 9B are examples of a field before and after the nitrogen prescription was executed on the field, respectively.
Figure 9B:
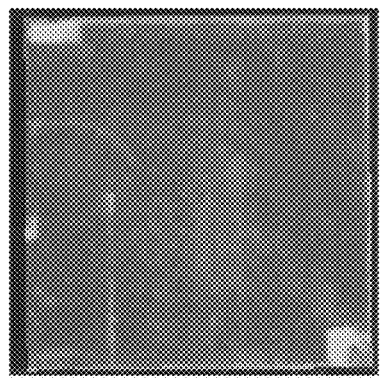

First, the technology can analyze a host of nitrogen-related variables (e.g., soil parameters, weather parameters, etc.) to determine nitrogen change for plants in analysis zones (e.g., geographic sub-regions, geographic regions, etc.). For example, the technology can leverage crop stressor data and/or remote imagery (e.g., satellite imagery from which vegetative performance can be extracted) to predict current and future growth stages for the analysis zones, which can function to determine the variance in a crop's nitrogen consumption, depending on growth stage. Nitrogen change can be used to develop nitrogen prescriptions for each geographic sub-region of a field. Nitrogen prescriptions can include a nitrogen application rate, amount, timing, location, or any other suitable nitrogen application parameter. The nitrogen prescription can be prescribed to optimize yield (e.g., as shown in FIGS. 9A-9B) or to obtain any other suitable goal or target.

Second, the technology can provide technical solutions necessarily rooted in computer technology (e.g., computationally calibrating modules, such as the crop module, with specialized datasets in an iterative process) to overcome issues specifically arising with the computer technology (e.g., improving accuracy for predicting growth stages and/or optimal nitrogen prescriptions, improving prediction speed, etc.). For example, a crop module (e.g., for determining growth stage for plants within an analysis zone) can be calibrated by comparing crop parameter outputs (e.g., from the crop module) to indirect measurements of the crop parameters. In a specific example, the leaf area index (LAI), determined from a vegetative performance value (e.g., wide dynamic range vegetative index), can be used as a validation value (e.g., used as ground truth for automated crop module calibration, such as parameter determination, equation determination, weighting value determination, etc.). However, the method can automatically generate any other suitable set of training data for module calibration, or otherwise update the modules.

Third, the technology can confer an improvement to the functioning of the nitrogen application equipment. Nitrogen prescriptions optimized for achieving crop goals can be used in generating control instructions for controlling agricultural equipment (e.g., equipment movement, orientation, nitrogen application timing, amount, rate, etc.) in applying nitrogen.

Fourth, the technology can effect a transformation of an object to a different state or thing. Nitrogen application equipment and/or other agricultural equipment can be activated and controlled according to control instructions determined, for example, based on nitrogen prescriptions. Digital imagery of a physical field can be transformed into physical nitrogen application to the physical field, which can subsequently result in physical crop yields and harvests. Crop fields can be transformed (e.g., from a nitrogen status anomaly state to a non-anomaly state; from a insufficiently fertilized state to a sufficiently fertilized state for reaching crop goals, etc.) in response to the nitrogen applied by nitrogen application equipment following control instructions.

Fifth, the technology can leverage specialized, non-generic computing device, such as fertilizer application equipment, seeding machinery, harvesting equipment, and/or other agricultural equipment, in performing non-generic functions, such as applying nitrogen according to a generated nitrogen prescription by executing control instructions; collecting specialized datasets for generating, updating, and or executing modules such as the nitrogen prescription module, or other functions.

The technology can, however, provide any other suitable benefit(s) in the context of using non-generalized computer systems for determining nitrogen change, generating nitrogen prescriptions, and/or implementing nitrogen prescriptions.

3. System

The system can include a crop module and a nitrogen change module. The system can additionally or alternatively include a total nitrogen module, nitrogen prescription module, management zone module, one or more computing systems configured to generate, execute, and/or update the one or more modules, agricultural equipment operable according to control instructions generated based on outputs of the one or more modules, or any other suitable component. The system functions to determine a nitrogen change over time (e.g., from a prior nitrogen application to a current time) for crops within a geographic region. The system can additionally or alternatively function to apply nitrogen to crops in accordance with one or more nitrogen prescriptions.

In a specific example of module use, nitrogen application information (e.g., treatment date, amount of nitrogen applied) is received from a farmer account at the total nitrogen module, where the total nitrogen module determines the amount of applied nitrogen available for each analysis zone (initial nitrogen amount). A set of historic remote images of the management region (e.g., 5 or more years of satellite images) is processed by the management zone module into a potential yield value for each analysis zone for each of a set of timeframes (e.g., recurrent timeframes, such as growth stages; non-recurrent timeframes, such as growing season times or calendar days; etc.), which cooperatively form a yield map depicting the relative potential of each analysis zone, compared to other analysis zones within the field. The initial nitrogen amount, potential yield, weather since nitrogen application (e.g., rainfall, wind, ambient temperature, growing degree day values, etc.), and soil data for each analysis zone is fed to the crop module, which estimates the growth stage for crops within each analysis zone. The growth stage, weather, and soil data are then fed into the nitrogen change module to determine the amount of nitrogen lost or gained from the analysis zone to date, where the initial nitrogen amount and amount of lost or gained nitrogen can be cooperatively used to determine the amount of nitrogen left within the analysis zone. A crop goal (e.g., crop yield, crop uniformity, minimum crop size, etc.) can be used to determine the amount of nitrogen needed to reach the crop goal (e.g., based on the current crop parameters, determined by the crop module, and a desired crop parameter), where the amount of nitrogen needed to reach the crop goal and the amount of nitrogen lost from (and/or amount of nitrogen remaining within) the analysis zone can be cooperatively used to determine the amount of supplemental nitrogen that should be applied to the analysis zone. The crop goal can be received from the farmer account, automatically determined based on market factors, automatically determined based on historic farmer preferences, or otherwise determined. The amount of supplemental nitrogen can be used with a nitrogen prescription module in determining a nitrogen prescription for each analysis zone (e.g., each geographic sub-region). However, the modules can be otherwise used.

System modules can include any of a: process-driven module (e.g., equation based module; differential equation module), fuzzy network module, clustering module, unsupervised machine learning module (e.g., artificial neural network, association rule learning, hierarchical clustering, cluster analysis, outlier detection), supervised learning module, semi-supervised learning module, deep learning module, and/or any other suitable module leveraging any other suitable machine learning method, probabilistic approach, heuristic approach, deterministic approach, and/or any combination thereof. In an example, a system module (e.g., crop module) can include a process-driven differential equation module. In another example, the system module (e.g., a crop module) can include an artificial neural network including input neurons corresponding to values of image elements from an image (e.g., pixels of a received satellite image of a geographic region). However, the input neurons can correspond to any other suitable set of factor values. The inputs and/or features (e.g., parameters used in an equation, features used in a machine learning model, etc.) used in a module can be determined through a sensitivity analysis, received from other modules (e.g., outputs), received from a user account (e.g., from the farmer, from equipment associated with the user account, etc.), automatically retrieved (e.g., from an online database, received through a subscription to a data source, etc.), extracted from sampled sensor signals (e.g., images, etc.), determined from a series of sensor signals (e.g., signal changes over time, signal patterns, etc.), and/or otherwise determined.

Figure 11:
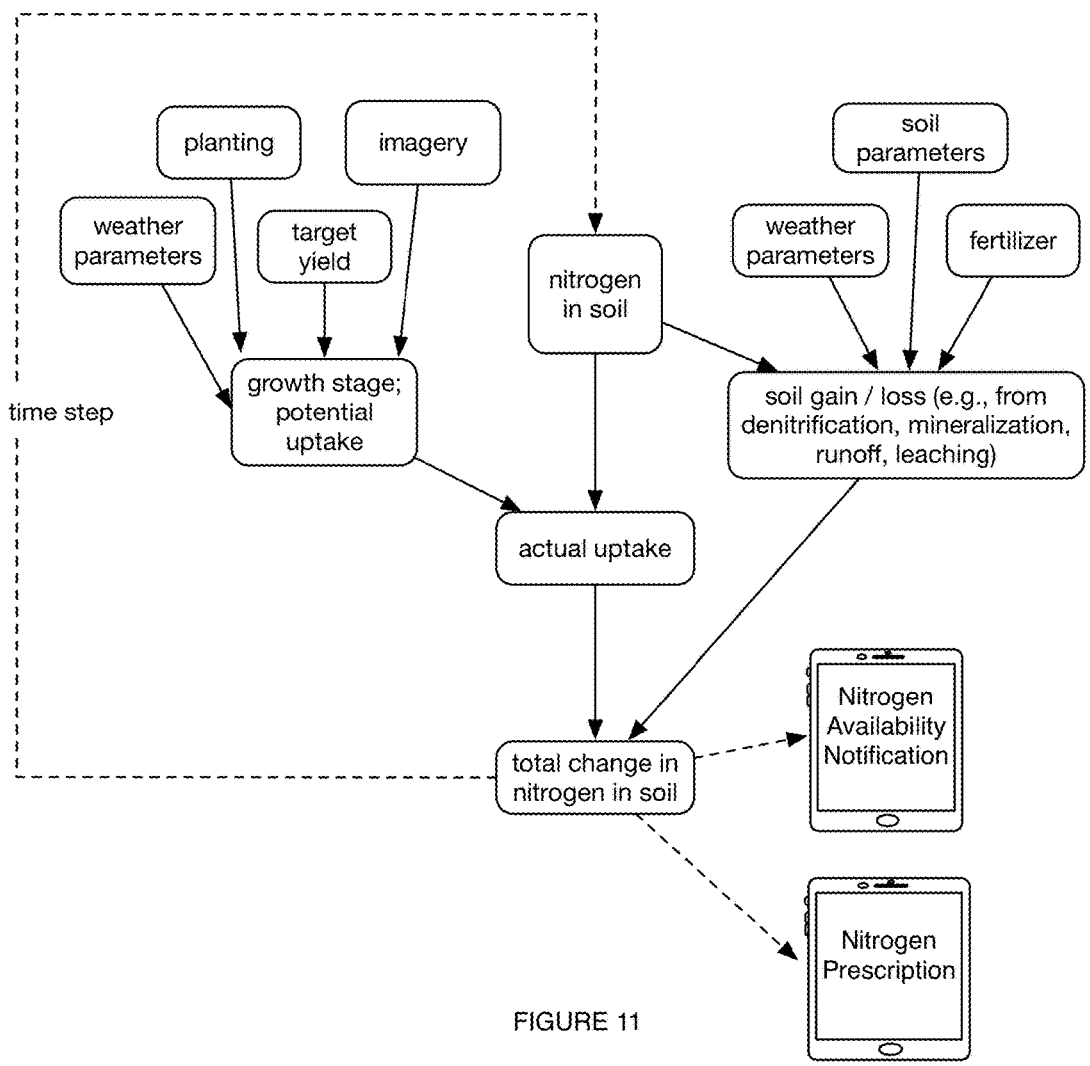
FIG. 11 is a schematic diagram of a variation of the method of remote nitrogen monitoring.

The modules are preferably universally used (e.g., the same models used across all user accounts, fields, and/or analysis zones), but can alternatively be specific to a cultivar, user account, field, analysis zone, or otherwise differ. Different instances of the method can be performed concurrently (e.g., in parallel), asynchronously, or at any other suitable time. Modules can be generated, executed, or calibrated every time the method is performed (e.g., based on up-to-date information), once, at a time interval (e.g., every day, week, month, etc.), every time a newly-received data value differs from a predicted data value; and/or at any other suitable frequency. Inputs and/or outputs of the modules can be associated with any suitable temporal indicator (e.g., daily data, averages over a period of time, etc.). Additionally, any suitable inputs for a module (e.g., crop module) can be used as inputs for another module (e.g., nitrogen change module), and any suitable outputs of a module can be used as inputs for another module. In an example, one or more modules and/or combination of modules of the system can be a time series module (e.g., where the output of a module at a first time can be used as an input to a same or different module at a second time, etc.). In a specific example, as shown in FIG. 11, an initial nitrogen availability in the soil can be adjusted by a calculated nitrogen uptake and soil gain/loss to obtain a total change in nitrogen in the soil for a first time, and the estimated nitrogen in the soil at the first time (e.g., day 1) can be used as the initial nitrogen availability in the soil at a second time (e.g., day 2). In another specific example, soil release data for the year preceding the current planting year is run through the nitrogen change module to determine the initially available nitrogen. In another specific example, as shown in FIG. 11, the method 100 can include determining a growth stage at a first time for plants within the geographic region using a crop module (e.g., with input parameters derived from remote monitoring data); determining a first nitrogen change for the geographic region based on the growth stage using a nitrogen change module; estimating a first nitrogen availability for the geographic region at the first time based on the first nitrogen change; repeating the preceding portions of the method 100 for a second nitrogen availability for the geographic region at a second time based on a second nitrogen change and the first nitrogen availability. In another specific example, the crop module and/or other suitable modules can be executed and/or updated at a predetermined time interval (e.g., daily) based on median weather for a representative year and historic weather for the growing season. However, repeating portions of the method 100 can be performed in any suitable manner.

The method can be applied to a single crop type or cultivar (e.g., corn, soy, alfalfa, wheat, rice, sugarcane, etc.), multiple crop types or cultivars, or any other suitable number of crop types and/or cultivars. In one variation, a different instance of the method (including different modules, module variants, factors considered, or other parameters) can be applied to each different crop type. The different method instances can be updated based on data associated with the respective crop type, or can be updated based on data from other crop types. In a second variation, the same instance of the method can be applied to multiple crop types. However, different instances of the method can be applied to any suitable number of crop types, related in any suitable manner, and otherwise updated.

The method can be applied to one or more analysis zones (e.g., field or field sub-region). Each analysis zone can include one or more crop types. In one variation, a different instance of the method (including different modules, module variants, factors considered, or other parameters) can be applied to each different analysis zone. The different method instances can be updated based on data associated with the respective analysis zone, or can be updated based on data from other analysis zones. In a second variation, the same instance of the method can be applied to multiple analysis zones. However, different instances of the method can be applied to any suitable number of analysis zones, related in any suitable manner, and otherwise updated.

The crop module of the system functions to determine the growth stage of the crop. The growth stage can subsequently be used to determine crop parameters, such as LAI, nitrogen consumption, nitrogen fixation, or any other suitable crop parameter. The growth stage or crop parameter values can be determined for: a reference time, a growth stage, an analysis time (e.g., past, current, or future), and/or for any other suitable temporal duration. The growth stage or crop parameter values can be determined, in relation to one or more zones (e.g., analysis zone, management zone, geographic sub-region, geographic region, field, etc.): for the population of crops; for each crop; for a model crop; as an average growth stage; as an average or model growth stage; and/or for any other suitable set of crops.

Features and/or inputs used in generating, executing, and or updating the crop module (or any other suitable module) can be include any one or more of: the planting date; crop cultivar; seed density or distribution (e.g., based on the seed rate, seed prescription, seeding equipment capabilities, etc.); prior crop growth stage; current crop growth stage (e.g., as received from a user, estimated from remote sensor measurements, etc.); historic crop growth stage for this time of the growing season; planting data; growing degree day values and/or other heat indexes; crop density coefficients (e.g., for specific hybrids); crop stressor data (e.g., weather parameters, soil parameters, topological parameters, historic vegetative performance values such as historic LAI, treatment history such as watering history and/or pesticide application history, disease history, pest history, crop anomaly history, etc.); remote monitoring data (e.g., date, time, solar angle, satellite angle, band values such as for blue, green, red, red edge, near infra-red, etc.); proxy map (e.g., yield proxy map); and/or any other suitable data that can influence crop growth. The planting data can include one or more of historic, current, and/or predicted: data, population (e.g., 33,000 seeds/acre), type (e.g., Po339AMXT, Pioneer, CRM: 99, Silk: CRM 95, GDUs to Silk: 1190, GDUs to Phy. Mat.: 2350, etc.). Weather parameters can include recorded, predicted, extracted, and/or otherwise obtained based on weather data or any other suitable data. The weather data can include one or more of: precipitation, min and/or max temperature, irradiance, sunrise time, sunset time, ambient temperature, soil temperature, frost, freeze, snow, tornadoes, rain, wind, or any other suitable weather data. Weather parameters and/or other suitable parameters can be aggregate parameters (e.g., averages, medians, etc.) calculated over any time period (e.g., median in-season rainfall for a preceding year, for a coming year, for a representative year determined from historic years, etc.). Soil parameters can be recorded, predicted, extracted, or otherwise obtained based on soil data or any other suitable data. Soil data can be by map unit (e.g., polygon) and/or horizon (e.g., layer), and can include one or more of: drain quality, pH, saturation or SAT, OC, SW, DUL, LL, soil layer composition, sand composition, silt composition, clay composition, organic matter composition, soil layer thickness, slope, wilting point, hydraulic conductivity, porosity, field capacity, initial soil water, soil bulk density, second stage evaporation coefficient for summer, cumulative evaporation before soil supply becomes limiting for summer, second stage evaporation coefficient for winter, cumulative evaporation before soil supply becomes limiting for winter, coefficient for calculating unsaturated unsaturated water diffusivity, slope for calculating unsaturated water diffusivity, runoff curve number for bare soil, maximum reduction in curve number due to surface cover, threshold of surface cover above which there is no effect on curve number, saturated soil drainage coefficient, carbon to nitrogen ratio for root, root growth factor, carbon to nitrogen ratio for soil, soil organic carbon content, fraction of biome pool carbon, fraction of inert pool carbon, nitrate concentration of the soil on a dry weight basis, or any other suitable soil data or parameter thereof. In an example, the set of crop module inputs can include: growing degree day values, nitrogen uptake, crop density coefficients for specific crop hybrids, and weather parameters (e.g., increased rainfall, leading to more nitrogen loss). In another example, the crop module inputs can include: crop defining factors (e.g., carbon dioxide, solar radiation, temperature, cultivar characteristics, etc.), growth limiting factors (e.g., water, nutrients), and growth reducing factors (e.g., weeds, pests, diseases, frost and extreme heat). However, any other suitable input can be considered. The data considered within the crop module is preferably data extending from the seeding date to the most up-to-date data (e.g., current data), but can alternatively be any other suitable set of data associated with any suitable temporal indicators. The parameters and/or data used by the crop module for analysis can be associated with the same time period (e.g., all characterize the analysis zone from May to October of the same year), be associated with different time periods, or be associated with any other suitable time periods that are related in any suitable manner. For example, weather data is preferably up-to-date, but the soil data can be historic data (e.g., collected before the growing season began). The inputs are preferably received from the user account (e.g., from the farmer, from equipment associated with the user account, etc.), but can alternatively be automatically determined (e.g., from an online database such as the Soil Survey Geography (SSURGO) database, received through a subscription to a data source, etc.), or be otherwise determined. In a specific example, the crop module can consider a subset of the aforementioned factors. For example, the crop module (or any other suitable module) can consider only DUL and SAT when determining the LAI value for the analysis zone. In this example, the crop module can include or feed outputs to a LAI determination module. The LAI determination module can consider the same or a different set of factors from those considered by the crop module. In this example, parameters of the LAI determination module (e.g., constants for the DUL and SAT factors, etc.) can be iteratively calibrated using image-derived LAI as the ground truth (e.g., where the image can be a remote image, such as satellite imagery or a RapidEye image, be a local image, or be any other image). However, the crop module can consider any suitable set of factors in determining the growth stage, LAI, or any other suitable crop parameter.

The crop module can output: the current crop growth stage, the historic crop growth stage, the current nitrogen requirement, the amount of nitrogen consumed, the predicted LAI, any other crop phenotype parameter values, and/or any other suitable information.

The crop module can be calibrated by a calibration module, where the calibration module can access the crop module parameters and/or equations, the most recent remote monitoring datapoint for the analysis zone, historic remote monitoring datapoints for the analysis zone, historic weather data for the analysis zone (e.g., for the instantaneous growing season, before the growing season, etc.), soil data for the analysis zone, user data for the analysis zone (e.g., information for the instantaneous growing season, such as planting date, cultivar, etc.; user preferences, etc.), and/or any other suitable information for crop module calibration. In a variation, the calibration module uses a shuffled complex evolution metropolis algorithm, and considers twenty or more parameters, but any suitable algorithm can be used.

The nitrogen change module of the system functions to determine the cumulative amount of nitrogen lost from the soil to: crops, nitrogen leaching (e.g., loss with soil water), denitrification, volatilization, soil erosion and runoff, and/or any other suitable loss channel. The nitrogen change module can additionally or alternatively function to account for the amount of nitrogen gained in the soil, such as from nitrogen release (e.g., by organic matter such as dead plant cells, microorganisms, mineralization, etc.). The nitrogen change module can include a nitrogen loss module (e.g., for outputting nitrogen loss from the soil such as from crop uptake, etc.), a nitrogen gain module (e.g., for outputting nitrogen gained in the soil such as from soil release, etc.), and/or any other suitable nitrogen change parameter. Features and/or inputs used in generating, executing, and or updating the nitrogen change module can include any one or more of: crop growth stage (e.g., historic, current, predicted), crop stressor data (e.g., same or distinct from crop stressor data used by other modules), weather parameters, soil parameters (e.g., nitrogen soil release based on soil types, etc.), fertilizer parameters (e.g., application information, fertilizer types, etc.), terrain maps, adjacent analysis zones and relationship to the respective analysis zone (e.g., where runoff from a more elevated adjacent zone can increase the amount of available nitrogen in the instantaneous zone), and/or any other suitable data that can influence nitrogen change. The features and/or inputs can be determined (e.g., calculated, extracted, etc.) from user inputs (e.g., equipment feeds, user entries), data feeds (e.g., remote images, weather model outputs, soil surveys, social media, markets, etc.), system modules (e.g., crop module, nitrogen loss module, nitrogen release module, etc.), or from any other suitable data source. The nitrogen change module can output the amount of nitrogen change (e.g., change since a previous nitrogen application, change over the growing season to date, change over a defined time period, etc.), rate of nitrogen change, nitrogen change for different types of nitrogen fertilizer (e.g., anhydrous ammonia, urea, urea-ammonium nitrate solutions, etc.), residual amount of nitrogen leftover from an initial nitrogen application (e.g., from a preceding year), an estimated amount of available nitrogen for plants within a zone at a given time, and/or other suitable nitrogen change parameters. For example, the growth stage (e.g., for determining crop uptake of nitrogen) and crop stressor data (e.g., rainfall) for the analysis zone can be used as an input into the nitrogen loss module to output a nitrogen loss in the soil. In another example, weather parameters, soil parameters, and fertilizer parameters can be input into the nitrogen gain module to output an amount of nitrogen gained in the soil (e.g., due to soil release). In another example, nitrogen release data (e.g., determined based on the SSURGO database, weather parameters, soil parameters, and/or other module inputs or outputs) and nitrogen loss data (e.g., determined based on the SSURGO database, weather parameters, soil parameters, and/or other module inputs or outputs) collected over a year can be input into nitrogen change module to determine change in nitrogen in the soil since an initial nitrogen application (e.g., determined from the total nitrogen module). Nitrogen change can be for each analysis zone, nitrogen change for an analysis zone relative other analysis zones, and/or for any suitable region.

The system can additionally or alternatively include a nitrogen prescription module, which functions to determine the amount of nitrogen to be applied to the crop during side-dress (e.g., after the crop has grown beyond a predetermined growth stage). In a first variation, the nitrogen prescription module determines the amount of nitrogen that should be supplemented (nitrogen supplement) to achieve a predetermined crop metric (e.g., size, weight, density, bushel volume, etc.) for each analysis zone. In a second variation, the nitrogen prescription module determines the rate of nitrogen application (e.g., how much nitrogen should be applied when and/or where) to achieve the nitrogen supplement. In a third variation, the nitrogen prescription module determines the ideal time for side-dress.

Features and/or inputs used in generating, executing, and or updating the nitrogen prescription module can be include any one or more of: the nitrogen change (e.g., nitrogen loss, nitrogen release, etc.), the current available nitrogen (e.g., from the nitrogen change module), the target nitrogen amount (e.g., as determined from crop goals), remote monitoring data, nitrogen stress (e.g., determined from correlation with green reflectance of remote monitoring data, etc.), time remaining in the growing season, the crop growth stage (e.g., current, predicted, historic), crop goals, and/or any other suitable data for the analysis zone. The target nitrogen amount can be: the amount of nitrogen needed to meet a crop goal (e.g., to meet a yield goal, which can be determined by the crop module or any other suitable module), less the amount of nitrogen currently available; the initial nitrogen amount (e.g. initial amount of nitrogen applied to the analysis zone); a user-specified nitrogen amount, and/or be any other suitable nitrogen amount. In a specific example, the target nitrogen amount can be calculated for each zone by multiplying the target yield for the zone by a state-specific factor (e.g., N/bushels). The state-specific factor can be automatically determined (e.g., empirically, selected from a graph, calculated, etc.), specified by a user, calibrated, or otherwise specified. The state-specific factor can be determined based on the crop type, crop cultivar, target harvest growth stage, or be determined based on any other suitable parameter. The target nitrogen amount can be determined by the nitrogen prescription module, crop module, a user application, and/or any other suitable module.

The nitrogen prescription module can output: the amount of nitrogen that should be supplemented (nitrogen supplement) for each analysis zone; a variable nitrogen application rate (e.g., a fixed rate per analysis zone, a variable rate over the analysis zone, management zone, or field, etc.), a fixed nitrogen application rate for the analysis zone, management zone, or field, or output any other suitable information. In one example, the nitrogen supplement can be the difference between the current nitrogen available and the target nitrogen for the analysis zone. However, the nitrogen supplement can be otherwise determined. The output can be a numerical file, a machine-readable file (e.g., for the nitrogen application equipment), or any other suitable output. When the nitrogen application rate is for the management zone or field, the nitrogen application rate can be optimized across the multiple analysis zones within the management zone or field to minimize cost, maximize yield, or achieve any other suitable goal.

The nitrogen prescription module can be generated, executed, and/or updated: in response to receipt of a prescription request for a nitrogen prescription, in response to determination that the farmer should side-dress the field, at a predetermined frequency, and/or at any suitable frequency.

The system can additionally or alternatively include a total nitrogen module, which functions to determine the amount of nitrogen available (e.g., at the beginning of a growing season, for a given time point, etc.) within each analysis zone. The determined available nitrogen is preferably specific to a time or time period, but can be associated with any other suitable time duration. The available nitrogen can be determined at and/or for: pre-planting, post-planting (e.g., within a predetermined period post-planting), throughout the growing period (e.g., beginning of the growing period, periodically, in response to occurrence of a determination event, such as nitrogen prescription generation, a predetermined growth stage being met, or nitrogen application), after harvest, or at any other suitable time. The available nitrogen is preferably associated with the time at which the available nitrogen amount is determined, but can be associated with the time(s) associated with the underlying data from which the available nitrogen amount is determined, the time associated with the most up-to-date underlying data from which the available nitrogen amount is determined, or associated with any other suitable time. The initial amount of nitrogen (e.g., total amount of nitrogen available at the beginning of a growing season) is preferably determined after nitrogen application to the analysis zone (e.g., nitrogen application to the field), but can alternatively be determined at any other suitable time. Features and/or inputs used in generating, executing, and or updating the total nitrogen module can be include any one or more of: the nitrogen application information for the analysis zone (or the management field), the nitrogen history of the analysis zone (e.g., from prior applications, prior crops, etc.), nitrogen change module output (e.g., nitrogen gain from the nitrogen gain module and/or nitrogen loss from the nitrogen loss module, etc.), and/or any other suitable nitrogen information. The nitrogen application information, nitrogen history, or other nitrogen information (e.g., soil data, weather data, etc.) are preferably received from the user account (e.g., from the farmer, from equipment associated with the user account, etc.), but can alternatively be otherwise determined. The nitrogen application information can include: the time of nitrogen application (e.g., date, hour, etc.), the amount of nitrogen applied (e.g., directly received or indirectly determined from the fertilizer type, fertilizer brand, fertilizer nitrogen concentration, fertilizer nitrogen type, etc.), the application equipment information, or any other suitable information. The total nitrogen module can output: the total nitrogen available to the crops for each analysis zone; the additional nitrogen available to the crops for each analysis zone, or any other suitable information. The total nitrogen module can be generated, executed, and/or updated every growing season (e.g., after crop harvest, after crop yield is determined, etc.); every time a new nitrogen treatment is performed on the field; and/or at any other suitable frequency.

The system can additionally or alternatively include a management zone module (e.g., productivity zone module), which functions to determine analysis zones for yield analysis, nutrient analysis, nutrient prescription, or any other suitable application. An analysis zone is preferably a geographic sub-region of a field (e.g., a field belonging to an entity or undergoing substantially the same treatment at substantially the same time), but can alternatively be any other suitable region (e.g., a geographic region, an entire field, etc.). An analysis zone is preferably represented in a received image (e.g., a satellite image of a 5 m by 5 m projected geographic region). Received images can partially or fully capture one or more analysis zones, regions related to analysis zones (e.g., soil regions adjacent an analysis zone, geographic regions surrounding an analysis zone, etc.), and/or any suitable region. An analysis zone can be determined based on any suitable management zone module inputs, such as remote monitoring data, nitrogen loss or gain (e.g., output from nitrogen change module), growth stage (e.g., output from crop module, etc.), and/or any other suitable inputs, such as soil zones, as further described below. Any number of image elements (e.g., pixels, superpixels, pixel sets or clusters, digital values, image segments, etc.) of a received image can be mapped to any number (e.g., a plurality) of analysis zones (e.g., geographic sub-regions in a geographic region). In one variation, each the geographic region represented by a pixel in a remote image is treated as an analysis zone. In a second variation, continuous geographic regions sharing a common parameter set (e.g., crop type, crop growth rate, etc.) are treated as an analysis zone. However, the analysis zones can be otherwise defined. Any number of image elements (e.g., pixels, superpixels, pixel sets, digital values, image segments, etc.) of a received image can be mapped to any number (e.g., a single, plurality) of any suitable region types. Received images are preferably associated with a temporal indicator (e.g., a specific time, a recurrent time, a time period, etc.), but can alternatively be time-agnostic (e.g., a computationally generated reference image, etc.). Additionally or alternatively, analysis zones can be otherwise represented (e.g., as a set of digital values, coordinates, other location indicators, etc.). Examples of nutrients considered for analysis (e.g., chemical compounds, chemical elements, etc.) can include: nitrogen, nitrogen compounds (e.g., organic nitrogen, inorganic nitrogen, etc.), phosphorous, potassium, limestone, vitamins, minerals (e.g., micronutrients), macromolecules (e.g., proteins), and/or any other suitable chemical compound and/or molecule.

The management zone module can additionally function to determine management zones, which are formed from one or more contiguous analysis zones having a substantially uniform yield, vegetative index per reference time (e.g., WDVRI value for June), or sharing any other suitable yield or crop growth characteristic (e.g., when substantially the same management practices have been applied across the analysis zone and/or the field), but the management zone can be otherwise defined. The management zone module can additionally determine the predicted yield, vegetative index, or other crop parameter value for each analysis zone for each of a set of reference times, and create a map depicting the relative values of the analysis zones (e.g., yield proxy maps, vegetative index proxy maps, etc.).

These proxy maps can additionally be used to generate seeding prescriptions, wherein a seeding parameter (e.g., seeding rate, seed density, etc.) is determined for each analysis zone. In one variation, more seeds are prescribed for higher yield analysis zones, while less seeds are prescribed for lower yield analysis zones. The seed parameter (e.g., number, deposition rate, etc.) can be determined for each zone using a neural network, a rule-based decision making module, selected from graph or chart based on a yield metric (e.g., based on the anticipated yield, yield score, etc.), calculated based on a yield metric for the zone, or otherwise determined based on any other suitable parameter. In a second variation, the seed density per analysis zone can be optimized based on the proxy map. However, the seed prescriptions can be determined in any other suitable manner. The seeding prescription can be automatically sent to the user, seeding equipment, or to any other suitable endpoint.

Features and/or inputs used in generating, executing, and or updating the management zone module can be include any one or more of: remote monitoring data (e.g., satellite images) for the analysis zones recorded over a predetermined duration of time (e.g., 5 years); field boundaries (e.g., a geofence, received from the farmer, extracted from county records, or otherwise determined; coordinates, etc.); soil data; nitrogen loss from a nitrogen loss module; nitrogen gain from a nitrogen gain module; other nitrogen change module outputs; growth stage (e.g., output from crop module, etc.); total nitrogen module outputs (e.g., available nitrogen at a given time point, etc.) any other suitable input indicative of historic yield for each of the set of analysis zones; any input and/or output of a module of the system; and/or any other suitable inputs. The management zone module can output: analysis zones (e.g., boundaries, coordinates, pixel identifiers, etc.); proxy maps (e.g., yield proxy maps, vegetative performance value proxy maps, etc.); an expected crop parameter value for a given reference time; and/or or any other suitable information. The management zone module can be generated, executed, and/or updated: in response to receiving an image and/or set of images; in response to a user request (e.g., for nitrogen change, for a nitrogen prescription, for control instructions to control nitrogen application equipment, etc.), or at any other suitable time. However, the modules of the system can be otherwise configured.

The system can additionally or alternatively include one or more computing systems, which function to generate, execute, and/or update the modules, store module-related data (e.g., modules, inputs, outputs, features, etc.) and/or user account data, or perform any other suitable functionality. In a first variation, a remote server manages all modules, and manages the computation for one or more analysis zones, exclusive of other analysis zones (which are handled by other servers). The server can locally store or otherwise access only the data relevant to the analysis zone (e.g., crop stressor data, past yield data, etc.). In a second variation, the computing system can include a cluster of servers. In a first sub-variant, each server within the cluster can specialize in a module, exclusive of the other modules. In a second sub-variant, the computation for all or a subset of the modules can be distributed across all servers. In a third variation, the set of servers include a set of resource servers, user account servers, and analysis servers. These servers are preferably stateless, but can alternatively be stateful or have any other suitable characterization. The set of resource servers can store persistent data, such as historic yield data (e.g., WDRVI, LAI, and satellite images); weather data; soil data; nitrogen profiles for different fertilizer types; crop module parameters for different cultivars; or any other suitable data used for nitrogen monitoring or prescription determination. The user account servers can store user account data, such as the geographic locations (e.g., geographic regions, geographic sub-regions, etc.) with which each user account (e.g., farmer) is associated; machines available to the farmer (e.g., seeding machines, nitrogen application machines, other agricultural equipment etc.); cultivar; yield goals; management data (e.g., planting date, treatment history, etc.); crop history; current crop parameters (e.g., as determined by the crop module); or any other suitable user-associated information. The user account data can be received from the user, be automatically determined (e.g., from secondary data received from the user or secondary sources, such as the satellite data), or be otherwise determined. The analysis servers can run the analysis modules, where the underlying data can be retrieved from the resource servers and/or user account servers.

Additionally or alternatively, the computing system can include processing components of a user device (e.g., laptop, desktop, tablet, smartphone, agricultural equipment, etc.), and/or other suitable component. However, computation and storage can be distributed in any other suitable manner across any suitable components. However, computing systems can be otherwise configured.

The system can additionally or alternatively include agricultural equipment, which functions to execute one or more nitrogen prescriptions and/or control instructions in facilitating nitrogen management for one or more geographic regions and/or sub-regions. Additionally or alternatively, the agricultural equipment can function to record crop-related measurements for use as features and/or inputs in generating, executing, and/or calibrating one or more modules. Agricultural equipment can include any one or more of: fertilizer (nitrogen, phosphorous, potassium, etc.) application equipment (e.g., applicators, stabilizers, spreaders, sprayers, fertigation systems, nurse tanks, etc.), seeding machinery, harvesting equipment (e.g., combine, reaper, thresher, winnower, etc.), and/or any suitable agricultural equipment. Agricultural equipment preferably operates according to control instructions (e.g., generated by a computing system based on a nitrogen prescription, etc.), but can additionally or alternatively operate manually in response to user input.

Crop-related measurements can include nitrogen data (e.g., nitrogen application, nitrogen availability, nitrogen change, etc.), crop stressor data, and/or any suitable data. In a variation, crop-related measurements can include sensor data sampled at agricultural equipment sensors and/or user device sensors, or include any other suitable data. The sensors can include any one or more of: mass flow sensors (e.g., crop flow sensors, grain flow sensors, etc.), pressure sensors, optical sensors, camera subsystem, motion sensors, or any other suitable sensor. Crop-related measurements are preferably recorded at agricultural equipment, but can additionally or alternatively be recorded at another user device (e.g., smartphone, tablet, smart watch, etc.), by an on-board system connected to the agricultural equipment, or by any other suitable system. Crop-related measurements are preferably transmitted to a remote server of the system, but can be otherwise communicated. However, agricultural equipment can be otherwise operated or configured.

4. Method

As shown in FIGS. 1-3, a method 100 for managing nitrogen within a geographic region includes: determining a growth stage for the geographic region using a crop module S110; and determining a nitrogen change for the geographic region, based on the growth stage, using a nitrogen change module S120. The method can additionally or alternatively include determining an amount of nitrogen initially available for the geographic region S122.

As shown in FIG. 1B, the method 100 can additionally or alternatively include determining a nitrogen prescription for the geographic region based on the nitrogen change using a nitrogen prescription module S130; generating control instructions for the nitrogen application equipment based on the nitrogen prescription S140; determining an updated module (e.g., an updated crop module, an updated nitrogen prescription module, etc.) S150; identifying a nitrogen status anomaly based on the nitrogen change S160; and/or presenting nitrogen-related information to a user account S170.

As shown in FIG. 2, the method 100 and/or portions of the method 100 can be performed any number of times at a predetermined frequency (e.g., every day, week, month, etc.), upon the occurrence of an analysis event (receipt of a remote monitoring datapoint, such as a satellite image of the analysis zone; receipt of a nitrogen request from user; etc.), and/or at any suitable time and/or frequency. The method 100 is preferably performed at a remote server and/or other computing system, but portions of the method 100 can be performed at any suitable component.

As shown in FIGS. 1-4 and 6, determining a growth stage for the geographic region using a crop module S110 functions to determine the phenology and/or nutrient requirements for the crops within an analysis zone for a given time (e.g., historic, current, predicted crop growth stage). The crop growth stage can be determined (e.g., estimated, calculated, etc.) for each crop within one or more analysis zones (e.g., each geographic sub-region of a plurality of geographic sub-regions), for a model crop representative of the crops within an analysis zone, for any suitable number of actual, physical crops within one or more analysis zones. The crop growth stage is preferably determined using the crop module, but can alternatively be received from the user (e.g., where the user physically visits one or more analysis zones and records the growth stage), and/or be otherwise determined. Similar or difference crop modules can be generated, executed, and/or calibrated for different crops, analysis zones, and/or any suitable component. In another example, the crop module is run for the field as whole, using the average, mean, and/or other aggregate measure of the seed, weather, soil, nitrogen, and/or other data.

Determining the growth stage is preferably based on a crop module and one or more received images. For example, a vegetative performance value determined based on one or more received images can be used in determining whether a crop is within a vegetative phase and/or reproductive phase, and a corresponding growth phase model can be used in predicting growth stage. In a specific example, determining the growth stage can include extracting a vegetative performance value for the geographic region from a received image; selecting a growth curve for the geographic region based on the vegetative performance value; and determining a transition date based on the growth curve; selecting a growth phase model (e.g., vegetative phase model, reproductive phase model, etc.) based on a current date and the transition date; and determining the growth stage based on the growth phase model. Additionally or alternatively determining the growth stage can be based on crop stressor data (e.g., without using image data) and/or any other suitable inputs and/or features. However, determining the growth stage can be performed in any manner analogous to that described in U.S. application Ser. No. 15/012,749 filed 1 Feb. 2016, and/or otherwise performed.

As shown in FIGS. 1-4 and 6, determining a nitrogen change for the geographic region using a nitrogen change module S120 functions to determine how much nitrogen has been lost (e.g., from crop uptake, rainfall, etc.) or gained (e.g., from soil release, etc.) over time (e.g., from initial nitrogen application to a given point in time) for one or more analysis zones. The nitrogen change for the geographic region is preferably determined based on the growth stage determined in S110, but can be otherwise determined.

The nitrogen change is preferably determined by the nitrogen change module, but can alternatively be determined by any other suitable module. Determining nitrogen change can be for any number of zones, using any number of nitrogen change modules. Additionally or alternatively, determining nitrogen change can be on a per-nitrogen fertilizer type basis (e.g., change of a first nitrogen fertilizer type, change of a second nitrogen fertilizer type), per-crop type basis, and/or determined along any suitable dimension. Determining nitrogen change can be performed in response to occurrence of an analysis event (e.g., determining a growth stage using the crop module; identifying a nitrogen status anomaly; receiving an image of the zone or region; etc.), at a predetermined frequency, and/or at any suitable time.

Determining nitrogen change is preferably based on growth stage for plants within one or more analysis zones, but can be otherwise determined. In a variation, the consumed nitrogen can be the nitrogen uptake required for the plant to get to the determined growth stage (e.g., a current growth stage, a future growth stage) from a historic time (e.g., a time of initial nitrogen application) and/or historic growth stage (e.g., determined and/or predicted by the crop module). The nitrogen uptake for one or more growth stages can be retrieved from a resource database (e.g., based on the growth stage, associated phenology, etc.), calculated (e.g., using the crop module), or otherwise determined. The nitrogen uptake required for the crop to grow from the previous growth stage to the current growth stage can additionally or alternatively account for crop stressor data during the analysis period, where the crop stressor nitrogen uptake can determined and added to the historic stage-to-stage nitrogen uptake for the crop. However, the nitrogen uptake for the crop can be otherwise determined.

Additionally or alternatively, determining nitrogen change can be based on environmental effects (e.g., due to crop stressors, denitirification, leach, runoff, volatilization, conditions converting nitrogen to other, crop-inaccessible nitrogen compounds, etc.) Determining the nitrogen change due to environmental effects can include: determining crop stressor values and modeling the nitrogen change based on the crop stressor values. For example, the nitrogen uptake required for the crop to grow from the previous growth stage to the current growth stage can additionally account for crop stressor data during the analysis period, where the crop stressor nitrogen uptake can determined and added to the historic stage-to-stage nitrogen uptake for the crop, but the nitrogen uptake for the crop can be otherwise determined. The crop stressor data that are determined are preferably measurements recorded (e.g., by agricultural equipment, a third party, a user device, etc.) during the intervening time period (e.g., from the initial nitrogen application time till the given time; from the given time for the last nitrogen change analysis to the current time; etc.), but can alternatively be any other suitable data.

As shown in FIGS. 1A and 2-3, the method can additionally or alternatively include determining an amount of nitrogen initially available S122, which functions to determine a starting value for nitrogen change determination. Nitrogen initially available can be determined for each zone (e.g., analysis zone, management zone), for the field as a whole, and/or any suitable region. The amount of nitrogen initially available is preferably determined based on the amount of applied nitrogen, and can additionally be determined based on the nitrogen history of one or more zones (e.g., based on the past crops grow; based on historic nitrogen prescriptions applied; etc.) or be determined based historical user input, data feeds, amount of applied nitrogen, features and/or inputs mentioned above, or based on any other suitable information. The amount of nitrogen initially available can be determined by the total nitrogen module, and/or any other module. The amount of nitrogen initially available within each analysis zone is preferably determined upon receipt of the nitrogen application information, but can alternatively be performed at any other suitable time.

As shown in FIG. 1A, the method can additionally or alternatively include receiving information indicative of nitrogen application for one or more zones S124. The information can be used to determine a starting date for nitrogen change determination, be used to determine the amount of nitrogen initially available S122, or be otherwise used. The information indicative of nitrogen application can include: the nitrogen application date, fertilizer type, fertilizer amount, fertilizer density, fertilizer application rate, fertilizer brand, fertilize volume, other indirect nitrogen indicator (e.g., received in lieu of a nitrogen mass measure), the prior crop in the zone, the planting date, cultivar, seed distribution across the zone (e.g., row spacing, seed rate and one or more seeding implement locations, etc.), historic nitrogen prescriptions, historic control instructions, crop goals (e.g., yield, number bushels, mass, crop shape, crop morphology uniformity, etc.), side-dress dates, crop-related measurements (e.g., sensor measurements) from agricultural equipment, nitrogen application equipment parameters (e.g., variable rate treatment capabilities, maximum and minimum application rates, maximum and minimum traversal rates, etc.), images of the zone, vegetative performance values (e.g., WDRVI, LAI, etc.), automatically transmitted to a computing system by equipment associated with the user account (e.g., the seeding equipment, fertilizer application equipment, user devices such as a smart phone, etc.), and/or any other suitable information. The information can be received from the user (e.g., in response to a query), retrieved from a database (e.g., based on a data identifier, such as a nitrogen application equipment identifier, fertilizer identifier, etc.), received by a third party, and/or otherwise determined. In a first example, the method 100 can include receiving sensor measurements of the nitrogen application equipment, the sensor measurements sampled during a historic time; automatically determining an initial nitrogen amount for the geographic region at the historic time based on the sensor measurements (e.g., from mapping sensor values to nitrogen amount; from using a machine learning model with sensor measurements and supplemental data such as crop stressor data; etc.); and determining the nitrogen change between the historic time to the first time based on the initial nitrogen amount. In a second example, the method 100 can include receiving a first image of the geographic region, the first image corresponding to a first time (e.g., prior to planting); extracting one or more vegetative performance values for the geographic region; and determining an amount of nitrogen initially available for the geographic region based on the vegetative performance value (e.g., by evaluating weed growth in the geographic region at the first time). In a third example, determining the amount of nitrogen can include calculating the amount of nitrogen initially applied based on the concentration of inorganic nitrogen within the fertilizer (e.g., retrieved from the resource server set based on the fertilizer identifier) and the volume of fertilizer applied (e.g., where the rate is received from the equipment or the volume is entered by the farmer, etc.). In a fourth example, determining nitrogen initially available can include modeling fertilizer runoff based on terrain (e.g., relative positions of the analysis zones), modeling fertilizer transport based on environmental factors during nitrogen application (e.g., wind, rain, etc.), and/or otherwise accounting for initial fertilizer travel.

In a first variation, determining the amount of nitrogen initially available includes dividing the amount of nitrogen applied to the field by the number of analysis zones. In a second variation, determining the amount of nitrogen initially available in each analysis zone includes dividing the total amount of fertilizer applied to the field by a unit area (e.g., 1 meter squared). In a third variation, determining the amount of nitrogen initially available in each analysis zone can include calculating the amount of nitrogen applied to each analysis zone, based on the estimated time at which the fertilizing apparatus was collocated with the analysis zone and the fertilizer application rate at that time. In a fourth variation, determining the amount of nitrogen initially available in each analysis zone can include calculating the amount of nitrogen applied to each analysis zone, based on the nitrogen application rate, recorded by the fertilizing apparatus, at one or more geographic locations within the analysis zone. However, the amount of nitrogen initially available in each analysis zone can be otherwise determined.

Figure 8:
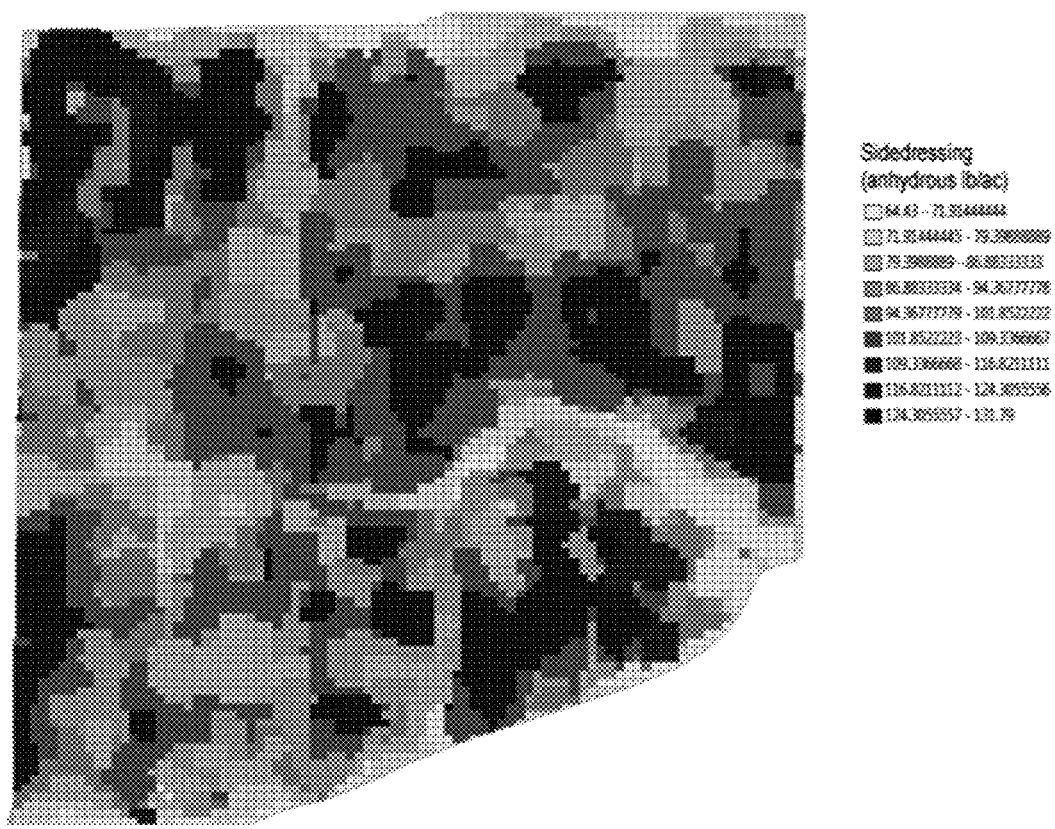
FIG. 8 is a schematic representation of an example of a nitrogen prescription.

As shown in FIGS. 1-4 and 6, the method 100 can additionally or alternatively include determining a nitrogen prescription S130, which functions to determine the amount of nitrogen to apply to one or more zones. Determining a nitrogen prescription can additionally or alternatively include determining the nitrogen requirements to achieve a crop goal S132 and/or determining a nitrogen application time S134. The nitrogen prescription is preferably tailored to optimize the yield, but can alternatively or additionally be tailored to obtain a different crop goal (e.g., crop uniformity such as homogenizing yield across the field, minimize nitrogen waste, volume, individual crop size, minimize cost, target crop growth stage, target crop parameters, etc.) and/or be otherwise optimized. The nitrogen prescription can be used for: initial nitrogen application, side-dressing (e.g., nitrogen application during a crop growth stage between VE to R6), or at any other suitable time. The nitrogen prescription is preferably determined using the nitrogen prescription module, but can alternatively determined by any other suitable module. Nitrogen prescriptions (e.g., including nitrogen requirements for achieving crop goals, nitrogen amount, application rate, etc.) can be determined (e.g., using the nitrogen prescription module) for any number of zones (e.g., as shown in FIG. 8). For example, determining nitrogen prescriptions (e.g., with a single nitrogen prescription module) can be for each geographic sub-region of a plurality (e.g., based on nitrogen change for each geographic sub-region). The nitrogen prescription is preferably determined upon receipt of a prescription request from a user, but can alternatively be determined at any other suitable time (e.g., at a date prior to scheduled nitrogen application; in response to determining a nitrogen change; etc.).

In a first variation, determining the nitrogen prescription can be based on a target yield (e.g., a yield goal). In a first example, determining nitrogen prescription can include determining the nitrogen prescription based on predicted yield data and target yield data for the geographic region at a future time. In a specific example where the geographic region includes a plurality of geographic sub-regions, the predicted yield data can include predicted yields for each geographic sub-region of the plurality, the target yield data can include target yields for each geographic sub-region of the plurality, and determining the nitrogen prescription can include determining sub-region nitrogen prescriptions for each geographic sub-region of the plurality based on differences between the predicted yields and the target yields. In a second example, the method 100 can include: receiving a yield goal for the field (e.g., 300 bushels of substantially uniform crop size distribution from this field), determining the distribution of target crop parameters across the analysis zones or management zones of the field (e.g., the first analysis zone should yield 10 bushels, while a second analysis zone should yield 2 bushels; determined based on the historic yield maps, based on an optimization analysis, etc.), determining the target crop growth stage or target crop parameters for each analysis zone at an estimated, future harvest time (e.g., received from the user, estimated, etc.), determining the current crop growth stage or current crop parameters for each analysis zone (e.g., based on recent satellite images, the crop module, etc.), and determining the mass of nitrogen supplement required to grow the corn from the current crop growth stage or crop parameters to the target crop growth stage or target crop parameters for each analysis zone. In a third example, the method 100 can include: receiving a yield goal for the field (e.g., 1,000 kg from this field), determining a target crop distribution across the analysis zones or management zones of the field, determining a current crop growth stage or current crop parameters for each analysis zone, determining the target crop growth stage or target crop parameters for each analysis zone at an estimated, future harvest time, based on a cost minimization analysis, and determining the nitrogen supplement mass required to grow the corn from the current crop growth stage or crop parameters to the target crop growth stage or target crop parameters.

In a second variation, determining the nitrogen prescription includes: applying more nitrogen to areas historically having higher yield (e.g., based on the yield proxy map), and applying less nitrogen (e.g., the minimum amount required to meet the crop goal) to areas historically having lower yield.

In a third variation, determining the nitrogen prescription includes: applying more nitrogen to areas estimated to have below-historic yield potential (e.g., based on the satellite images, crop module, etc.).

In a fourth variation, determining the nitrogen prescription includes: determining the initial nitrogen amount for each analysis zone, determining the amount of nitrogen left in each analysis zone, and determining the amount of nitrogen needed in each analysis zone to regain the initial nitrogen amount.

In a fifth variation, determining the nitrogen prescription can be based on user-selected preferences (e.g., types of nitrogen, supply of nitrogen, preferred range of amount of nitrogen application, preferred times of nitrogen application, etc.). For example, a user can input an amount of nitrogen and/or amount of money available, and a nitrogen prescription can be generated in accordance with the user-inputted limitations. However, the nitrogen prescription can be otherwise determined.

The nitrogen prescription can be: a nitrogen mass, a nitrogen application rate for the field (e.g., a constant nitrogen application rate), a nitrogen application rate for each analysis zone or management zone (e.g., a variable nitrogen application rate), nitrogen application for different types of nitrogen fertilizer, and/or be any other suitable measure of nitrogen mass or derivative thereof.

In a first variation, a nitrogen mass is determined for the entire field. In this variation, the nitrogen supplement masses for each constituent analysis zone within the field can be summed to obtain the nitrogen mass. However, the nitrogen mass for the field can be otherwise determined.

In a second variation, a constant nitrogen application rate is determined for the entire field. In one embodiment, the constant nitrogen application rate can be determined by dividing the nitrogen mass for the field (e.g., determined in the first variation or otherwise determined) by the equipment traversal distance. In a second embodiment, the nitrogen application rate for each analysis zone is determined, and the average or mean nitrogen application rate for the population of analysis zones is determined as the constant nitrogen application rate. In a third embodiment, the constant nitrogen application rate is an optimized rate based on the nitrogen supplement masses for each analysis zone or management zone within the field. However, the constant nitrogen application rate can be otherwise determined.

In a third variation, a variable nitrogen application rate is determined for the field, based on the respective nitrogen application rate or mass for each analysis zone or management zone within the field. In this variation, a different nitrogen application rate, determined based on the respective nitrogen supplement mass, is determined for each analysis zone. The nitrogen application rate can then be associated with: a geographic location associated with the analysis zone (e.g., within the analysis zone, immediately before the analysis zone to accommodate for actuation delay, etc.), an equipment traversal distance (e.g., first rate for the first 5 m; second rate for next 10 m), an equipment traversal rate, duration, and/or path (e.g., first rate for 10 minutes while operating the vehicle at 5 m/min; second rate for 20 minutes while operating the vehicle at 10 m/min), or otherwise associated with a direct or indirect geographic measure.

As shown in FIG. 1B, determining a nitrogen prescription can additionally or alternatively include determining the nitrogen requirements to achieve a crop goal (e.g., received by a user) S132, which can function to identify the nitrogen supplement to apply to one or more zones in obtaining one or more crop goals. In a first variation, the crop module (e.g., the most up-to-date crop module) and/or other module can be used to automatically estimate the nitrogen requirements to achieve the crop goal (e.g., target crop growth stage, target crop parameters). In this variation, crop stressors (e.g., weather parameters, soil parameters, etc.) can be forecasted (e.g., using machine learning modules, etc.) and/or otherwise determined for use in determining nitrogen requirements. In a second variation, the nitrogen requirements for the target crop growth stage, target crop parameters, and/or other crop goals can be selected or otherwise retrieved from a database (e.g., from the resource database), where the nitrogen supplement mass can include the difference in nitrogen requirements between the current growth stage or crop parameters and the target growth stage or crop parameters, in addition to a correction factor (e.g., constant, calculated, etc.) to accommodate for environmental nitrogen loss. In a third variation, the nitrogen requirements are directly received from a user. However, the nitrogen requirements for the target crop growth stage or crop parameters can be otherwise determined.

As shown in FIG. 1B, determining a nitrogen prescription can additionally or alternatively include determining a nitrogen application time S134, which can function to inform a user on when to apply nitrogen to the field (e.g., when to side-dress). The nitrogen application time is preferably a future time, but can alternatively be a current time or any other suitable time. Determining a nitrogen application time can include: determining (e.g., estimating) the nitrogen loss rate for each analysis zone, based on the estimated crop growth rate for each analysis zone and estimated (e.g., forecasted) crop stressor values for each analysis zone. The nitrogen loss rate can be extrapolated to identify when soil nitrogen should be supplemented. Additionally or alternatively, the nitrogen application time can be received from the user account or otherwise determined.

As shown in FIGS. 1-4 and 6, the method 100 can additionally or alternatively include generating control instructions for agricultural equipment S140 (e.g., fertilizer application equipment such as nitrogen application equipment, seeding machinery, harvesting equipment, etc.), which functions to generate instructions for controlling agricultural equipment to apply and/or facilitate application of nitrogen (e.g., according to one or more nitrogen prescriptions). The control instructions can include instructions for equipment movement, orientation, nitrogen application timing, amount, rate, and/or any suitable parameter and/or operation of agricultural equipment and/or associated devices. Determining control instructions is preferably based on a nitrogen prescription (e.g., control instructions direct the agricultural equipment to apply nitrogen according to parameters of the nitrogen prescription, etc.), but can be based on any outputs of any modules (e.g., nitrogen change), crop goals, crop-related measurements, and/or any other suitable data.

Determining control instructions can be performed in response to occurrence of an analysis event (e.g., generating a nitrogen prescription; a scheduled time prior to nitrogen application; user request for a prescription and/or control instructions; automatic request from the agricultural equipment, etc.), at a predetermined frequency (e.g., according to a fertilizer application schedule), and/or at any suitable time. Control instructions can be transmitted directly from a remote server to the agricultural equipment, to a user device (e.g., which can subsequently transmit the control instructions to agricultural equipment; which can present the control instructions to a user to manually implement with agricultural equipment, etc.). However, determining and/or transmitting control instructions can be performed in any suitable manner.

As shown in FIGS. 1-3 and 5-6, the method 100 can additionally or alternatively include determining an updated (e.g., calibrated) module S150, which functions to refine one or more modules in achieving more accurate outputs, faster execution (e.g., determination of outputs), faster retrieval of modules, and/or other suitable purposes. Determining an updated module can be based on one or more actual and/or predicted (e.g., expected): vegetative performance values (e.g., LAI), remote monitoring imagery (e.g., historic satellite imagery, current satellite imagery), maps (e.g., yield maps, nitrogen prescription maps, etc.), inputs and/or outputs of a module, and/or any suitable data. Determining an updated module can be performed for any number and/or type of modules (e.g., crop module, nitrogen change module, nitrogen prescription module, total nitrogen module, management zone module, calibration modules for any of the preceding modules, etc.), and any approaches usable in updating a given module (e.g., crop module) can be usable in updating a different module (e.g., nitrogen change module, etc.). Determining an updated module and associated portions of the method 100 are preferably iteratively performable and/or can be performed any number of times. For example, the method 100 can include: determining nitrogen change and/or a nitrogen prescription based on a first growth stage determined by a first crop module with a first image of the geographic region; receiving a second image of the geographic region; determining a second crop module (e.g., calibrating the first crop module) based on the second image; receiving a third image of the geographic region; and determining a second growth stage based on the third image using the second crop module. In another example, the method 100 can include repeating any suitable portions and/or steps of the method 100 using updated modules with same or different (e.g., newer) inputs. Alternatively, determining an updated module can be performed once. However, determining an updated module can be performed in any suitable manner.

Determining an updated module can be in response to occurrence of an analysis event (e.g., verification failure such as actual parameter vs. predicted output parameter from a module differing beyond a threshold; receiving a new remote monitoring datapoint (e.g., satellite image); receiving ground-truth data such as from agricultural equipment and/or user inputs; a user request such as a prescription request; etc.), at a predetermined frequency, and/or at any suitable time. In an example, a combination of modules (e.g., all system modules) can be updated in response to an analysis event being met for a single module (e.g., actual vs. predicted output for the crop module differing beyond a threshold, etc.).

Determining the updated crop module can include updating module equations, input types, features, considered factors, weights, and/or sub-modules; and/or otherwise adjusting the module. For example, determining an updated module can include through different permutations of the module until conditions for verification are satisfied (e.g., actual LAI substantially matches predicted LAI from a crop module, etc.). However, any suitable portion of a module can be updated.

Determining an updated module can additionally or alternatively include determining an updated crop module S152. The crop module can be calibrated in relation to an analysis event (e.g., before, after, or during crop growth stage determination; when nitrogen loss to crop uptake is determined; prior to calibrating a nitrogen prescription module, etc.) and/or at any suitable time. In a first variation, calibrating the crop module can be based on historic remote monitoring data (e.g., historic satellite imagery). In an example, determining an updated crop module can be based on a reference yield map for the geographic region. The reference yield map determined based on a set of historic images corresponding to historic instances of a recurrent time and/or any other suitable data. Values from the reference yield map can be compared to one or more outputs of the crop module and/or other modules. Additionally or alternatively, reference yield map can be used in calibrating any suitable module. However, calibrating the crop module can incorporate any approaches described in U.S. application Ser. No. 14/929,055 filed 30 Oct. 2015, which is hereby incorporated in its entirety by this reference.

In a second variation, calibrating the crop module can be based on vegetative performance values (e.g., WDRVI, LAI, etc.). Determining vegetative performance values in calibrating the crop module can be for any number of zones (e.g., where differences in actual vs. predicted vegetative performance values for geographic sub-regions can be aggregated and compared to a threshold aggregate difference). In a first example, determining an updated crop module can include generating a plurality of sub-region differences by calculating a sub-region difference between a sub-region actual LAI and a sub-region anticipated LAI for each geographic sub-region of a plurality; summing the plurality of sub-region differences; and comparing the sum to a threshold difference. In a second example, the method 100 can include receiving a remote monitoring datapoint captured at a first timestamp (e.g., a satellite image), determining a vegetative index (e.g., WDRVI) from the datapoint (e.g., from the satellite image colors), determining a measured LAI for groundtruth from the vegetative index; determining a calculated LAI using the crop module, based on crop stressor data up to the first timestamp; comparing the measured and calculated LAI area; and calibrating the crop module in response to the calculated and measured LAI differing more than a threshold amount. In a third example, the method 100 can include receiving an image (e.g., a first image used in determining a nitrogen prescription; a second image distinct from the first image; etc.) of the geographic region, the image corresponding to a time; determining an actual LAI (e.g., determined from a wide dynamic range vegetation index (WDRVI) value extracted from the image) for the geographic region based on the image; determining an anticipated LAI for the geographic region for the second time based on the first crop module and crop stressor data (e.g., weather parameter associated with the time, soil parameters, historic LAI extracted from an image corresponding to a historic time, etc.) sampled prior to the time; and determining a second crop module based on the actual LAI and the anticipated LAI. In a fourth example, the calculated LAI can be checked against on-the-ground measurements (e.g., received from the user account, equipment, etc.). In a fifth example, calibration can be in response to a difference between a predicted growth curve (e.g., predicted vegetative performance values over times) and an actual growth curve (e.g., determined based from satellite images, crop-related measurements from agricultural equipment, etc.). However, the crop module can be otherwise calibrated based on vegetative performance values.

In a third variation, updating the crop module can be based on growth stage (e.g., comparing predicted vs. actual growth stage). In an example, the method 100 can include determining a predicted growth stage for the geographic region at a time, using the crop module (e.g., with crop stressor data); determining an actual growth stage for the geographic region (e.g., manually with the leaf collar method, automatically from an image of the crop); and updating the crop module based on a difference between the predicted and actual growth stages.

In a fourth variation, updating the module can be based on a time difference between a predicted transition point (e.g., based on one or more remote monitoring datapoints preceding the transition point, etc.) and an actual transition point (e.g., based on crop-related measurements from agricultural equipment, based on user input, based on newly received remote monitoring datapoints, etc.) between vegetative and reproductive phases. However, determining an updated crop module can be otherwise performed.

Determining an updated module can additionally or alternatively include determining an updated nitrogen change module S154. Calibrating a nitrogen change module can be performed in relation to an analysis event (e.g., identifying a nitrogen status anomaly S170; prior to, during, and/or after determining a nitrogen change; etc.), and/or at any suitable time. In variations, determining an updated nitrogen change module can include comparing actual and predicted values for one or more of: nitrogen change over time (e.g., for one or more zones, for different types of nitrogen fertilizer, for one or more growth stages, etc.); nitrogen availability (e.g., over time, at an instantaneous time, etc.), and/or any other suitable parameters. Actual nitrogen change values can be determined from in-situ measurements or otherwise determined.

Determining an updated module can additionally or alternatively include determining an updated nitrogen prescription module S156. Updating the nitrogen prescription can be in relation to an analysis event (e.g., in response to a nitrogen prescription request from a user, after harvest, etc.), and/or at any suitable time. The nitrogen prescription module is preferably verified based on harvest data associated with the analysis zones, where the estimated crop parameter values for each analysis zone, determined based on the nitrogen prescription, can be compared against the actual crop parameter values from the harvest data. The harvest data can be collected by the combines or other harvesting equipment, entered by the user, or otherwise determined. The harvest data is preferably associated with a geographic identifier (e.g., set of coordinates, analysis zone identifier, etc.), but can alternatively or additionally be associated with any other suitable set of information. The geographic identifier can be associated automatically by the system (e.g., based on accelerometer data, data of harvesting equipment traversal over the field, etc.), automatically by the harvesting equipment, and/or otherwise associated with a geographic identifier. The geographic location associated with the harvest data can additionally be corrected for traversal delays between harvest and measurement.

In a variation, calibrating the nitrogen prescription module can be based on actual and predicted yields. For example, calibrating can include: determining a predicted yield for the crops based on the nitrogen prescription; determining an actual yield for the geographic region; and calibrating the nitrogen prescription module (e.g., a state specific factor for the module) based on a difference between the predicted yield and the actual yield. In another example, calibrating can include: determining the actual yield for each analysis zone based on the respective harvest data associated with geographic identifiers falling within the analysis zone; determining the estimated yield based on the nitrogen prescription and crop stressor data up to the harvest date (e.g., based on the crop module for the harvest date); comparing the estimated yield with the actual yield; and calibrating the nitrogen prescription module in response to the estimated yield differing from the actual yield by a threshold difference (e.g., by iterating through different model permutations until the estimated yield substantially matches the measured yield). Actual yield can be automatically determined from harvest data from harvesting equipment; determined based on vegetative performance values extracted for images preceding and/or after a scheduled harvest time; and/or otherwise determined. However, the nitrogen prescription module can be otherwise calibrated.

As shown in FIG. 1B, the method 100 can additionally or alternatively include identifying a nitrogen status anomaly (e.g., a nitrogen stress) S160, which functions to identify unexpected nitrogen statuses (e.g., unexpected nitrogen availability, unexpected nitrogen loss, etc.) of one or more zones, to catalyze presentation of the nitrogen status anomaly to a user at a user device and/or modification of the nitrogen prescription to accommodate one or more nitrogen status anomalies, and/or for any suitable purpose. Identifying nitrogen status anomalies (e.g., with a nitrogen anomaly module) can be based on crop stressors (e.g., weather parameters, soil parameters, pests, human interference, etc., crop inputs (e.g., changes in fertilizer application, changes in seeding, etc.), and/or any suitable variable. Any number and/or type of nitrogen status anomalies can be determined for any number of zones.

Identifying a nitrogen status anomaly is preferably in response to determining a nitrogen change (e.g., nitrogen loss, nitrogen gain, etc.), but can be performed in relation to any analysis event (e.g., determining a growth stage; identifying a crop health anomaly; responding to a user request for nitrogen status), and/or at any suitable time. Identification of nitrogen status anomalies can trigger performance of any suitable portion of the method 100 (e.g., generating a nitrogen prescription; determining an updated module, etc.).

In variations, identifying a nitrogen status anomaly can be based on one or more of: weather parameters, soil parameters, a difference in actual nitrogen availability (e.g., determined based on vegetative performance values extracted from satellite images; determine for an instance of a recurrent time; over time; etc.) vs. predicted nitrogen availability (e.g., determined with the nitrogen change module; determined with the total nitrogen module; determined for a recurrent time; over time; etc.); supplemental data (e.g., unexpected nitrogen availability given crop stressor data over the preceding month, etc.); a comparison of nitrogen-related information (e.g., expected differences in nitrogen availability and/or nitrogen change between zones, which can be determined from historic nitrogen-related information, etc.) for one or more zones (e.g., a geographic sub-region) and one or more associated zones (e.g., an adjacent geographic sub-region); a difference above a threshold value between an actual and predicted crop parameter (e.g., vegetative index) post-nitrogen application; and/or any suitable criteria. However, identifying a nitrogen status anomaly can be otherwise performed.

In a variation, identifying a nitrogen status anomaly can include determining a nitrogen stress based on reflectance values associated with remote monitoring data. Higher reflectance can be correlated with increased nitrogen stress, indicating that more nitrogen should be added to the region of stress. Nitrogen stresses and/or other nitrogen status anomalies can be an analysis event triggering determination of a nitrogen prescription to treat the nitrogen status anomaly. Determining nitrogen stress based on reflectance preferably includes evaluating predetermined wavelength ranges (e.g., 518-572 nm, 520-550 nm, 695-705 nm, 690-730 nm, etc.), wavelength ratios, and/or any suitable wavelengths. Wavelength ranges used for evaluation can be determined based on growth stage, crop hybrid or variety, and/or other suitable criteria. Analysis zones represented in the remote monitoring data can be classified (e.g., as a nitrogen stress region; with a nitrogen stress value indicating degree of nitrogen stress; etc.) based on reflectance thresholds (e.g., identifying a nitrogen stress if green reflectance exceeds a threshold reflectance), supplementary data (e.g., identifying nitrogen stress based on a combination of high green reflectance and increased rainfall, etc.), comparisons with historic reflectance values (e.g., identifying a nitrogen stress in response to a reflectance value for a current instance of a recurrent time point exceeding an expected reflectance value determined based on historic instances of the recurrent time point), and/or any suitable criteria. However, identifying nitrogen status anomalies based on reflectance values can be otherwise performed.

Identifying a nitrogen status anomaly can include selecting (e.g., prioritizing, filtering, etc.) zones to evaluate for nitrogen status anomalies. Selecting zones can be based on parameters (e.g., soil parameters, weather parameters, etc.) used in identifying a nitrogen status anomaly, supply availability (e.g., labor, fertilizer, supply location, supply amount, etc.), temporal parameters (e.g., time point in the growing season, etc.), remote monitoring data (e.g., newly available remote monitoring data, etc.), and/or any suitable criteria. In an example, selecting zones can include prioritizing zones for evaluating nitrogen status based on rainfall for a zone (e.g., 20% above average rainfall), labor supply availability (e.g., zones within 30 miles of contractors who can apply late season nitrogen), and/or remote monitoring data (e.g., zones with satellite imagery available for the previous two weeks). In another example, selecting zones can include receiving a rainfall parameter for the geographic region, the rainfall parameter associated; and in response to the rainfall parameter exceeding a historic rainfall parameter, evaluating nitrogen status for the geographic region based on the rainfall parameter and a reflectance for an image of the geographic region (e.g., an image used in determining growth stage and nitrogen change for estimating nitrogen availability), where determining a nitrogen prescription is in response to the nitrogen status indicating a nitrogen status anomaly (e.g., a nitrogen stress). However, prioritizing zones to evaluate for nitrogen status anomalies can be performed in any suitable manner.

Figure 7:
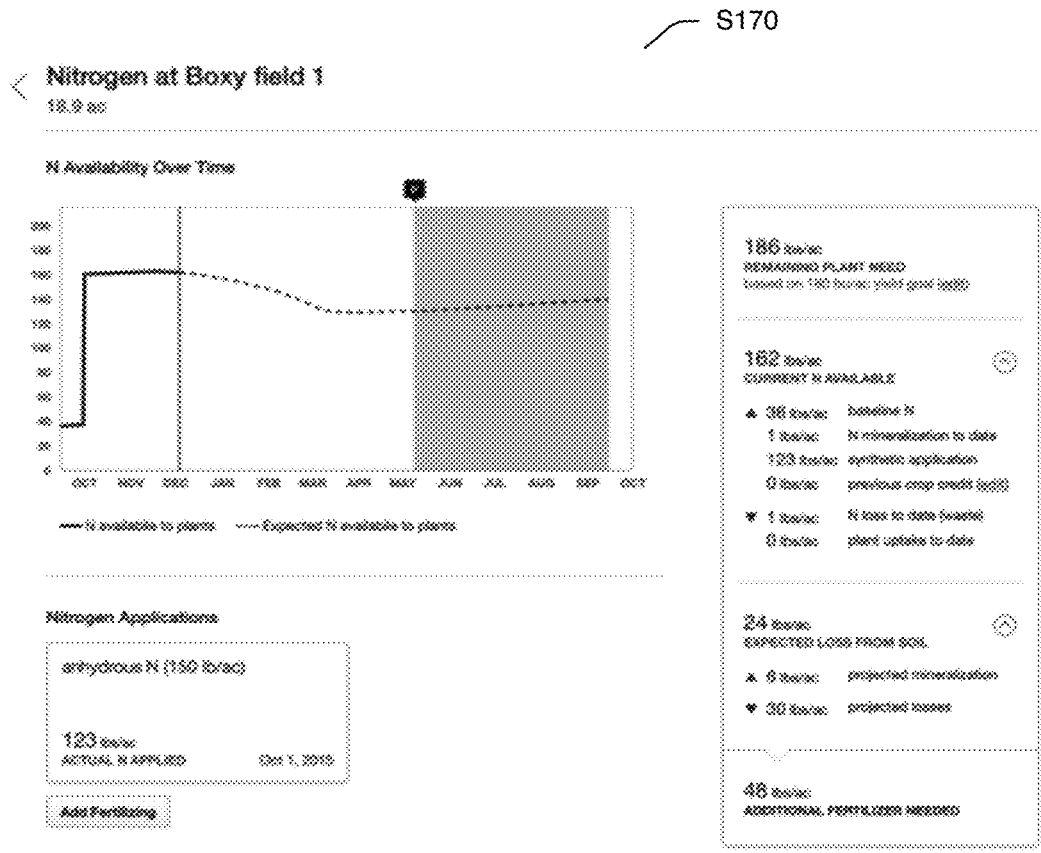
FIG. 7 is a schematic representation of an example of a user interface for presenting nitrogen availability over time.
Figure 10:
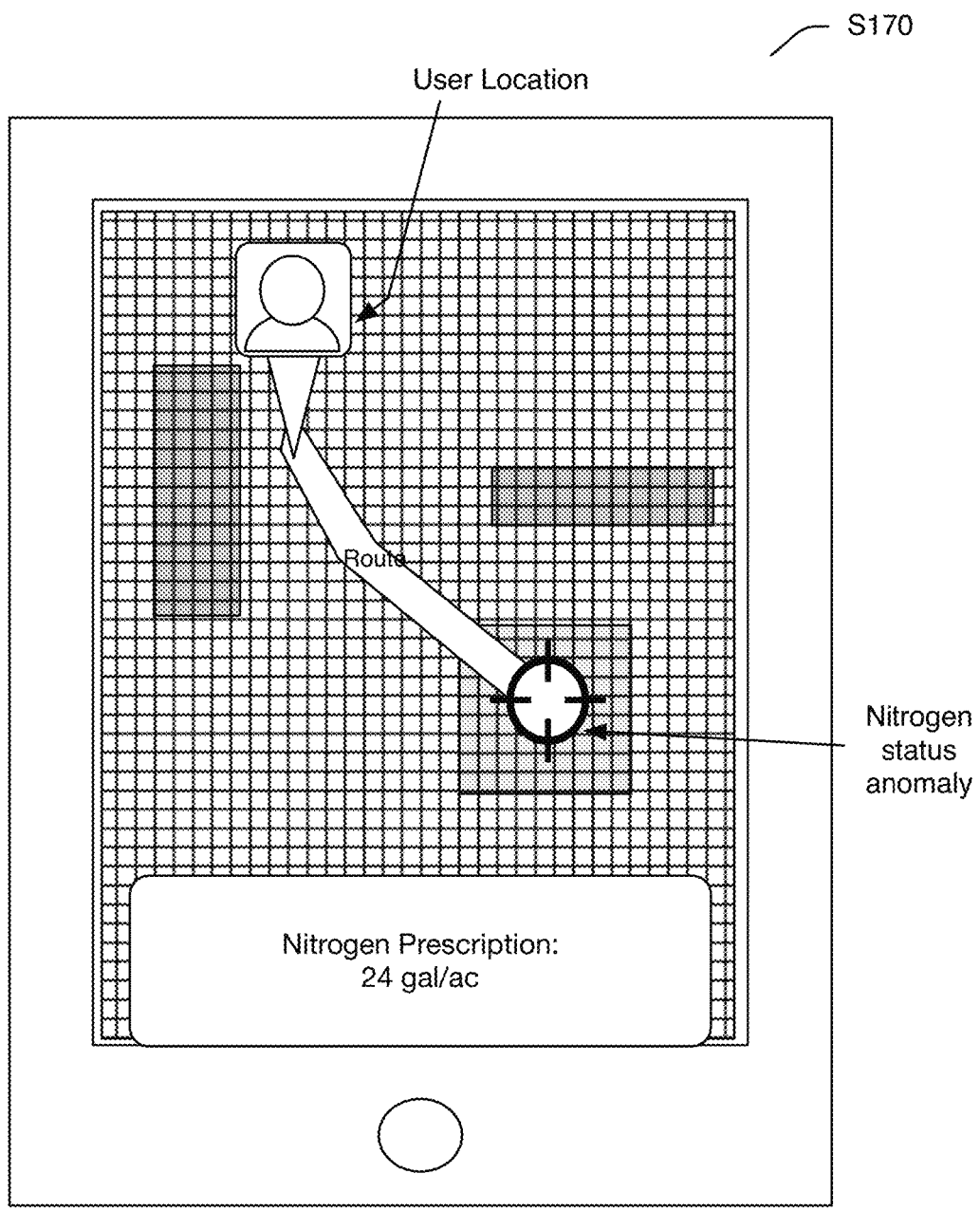
FIG. 10 is a schematic representation of an example of a nitrogen status anomaly notification.

As shown in FIGS. 1, 7, and 10, the method 100 can additionally or alternatively include presenting nitrogen-related information (e.g., nitrogen change, availability, prescriptions, status anomalies, etc.) to a user account (e.g., at a user device) S170, which functions to inform a user (e.g., a farmer) of the nitrogen-related information. A metric for how much nitrogen is left in their fields. Presenting nitrogen-related information can be presented as one or more of: a value, map (e.g., illustrating geographic sub-region nitrogen prescriptions), machine-readable file (e.g., control instructions automatically loaded onto agricultural equipment), notification, graphic, audio, video, and/or any suitable format. However, presenting nitrogen-related information can be otherwise performed.

An alternative embodiment preferably implements the above methods in a computer-readable medium storing computer-readable instructions. The instructions are preferably executed by computer-executable components preferably integrated with a nitrogen analysis system. The nitrogen analysis system can include a field system, crop modeling system, nitrogen change system, and a nitrogen prescription system. The computer-readable medium can be stored on any suitable computer readable media such as RAMs, ROMs, flash memory, EEPROMs, optical devices (CD or DVD), hard drives, floppy drives, or any suitable device. The computer-executable component is preferably a processor but the instructions can alternatively or additionally be executed by any suitable dedicated hardware device.

Although omitted for conciseness, the preferred embodiments include every combination and permutation of the various system components and the various method processes, where the method processes can be performed in any suitable order, sequentially or concurrently.

As a person skilled in the art will recognize from the previous detailed description and from the figures and claims, modifications and changes can be made to the preferred embodiments of the invention without departing from the scope of this invention defined in the following claims.

We claim:

1. A method for managing nitrogen within a geographic region, the method comprising:
   a) receiving a first image of the geographic region from an imaging system, the first image associated with a first time;
   b) determining a first growth stage at the first time for plants within the geographic region based on the first image using a first crop system;
   c) determining a first nitrogen change for the geographic region based on the first growth stage using a nitrogen change system;
   d) estimating a first nitrogen availability for the geographic region at the first time based on the first nitrogen change;
   e) repeating b) to d) for a second nitrogen availability for the geographic region at a second time based on a second nitrogen change and the first nitrogen availability;
   f) receiving a second image of the geographic region;
   g) determining a reflectance for the second image;
   h) identifying a nitrogen status anomaly for the geographic region based on the second nitrogen availability and the reflectance;
   i) in response to identifying the nitrogen status anomaly, determining a nitrogen prescription for the geographic region based on the second nitrogen availability using a nitrogen prescription system;
   j) generating first control instructions based on the nitrogen prescription, wherein nitrogen application equipment applies nitrogen according to the first control instructions;
   k) determining a reference yield map for the geographic region, based on a set of historic images corresponding to historic instances of a recurrent time;
   l) determining a second crop system based on the reference yield map and an output of the first crop system for the recurrent time; and
   m) generating second control instructions based on a third nitrogen availability, comprising: repeating b) to d) using the second crop system and repeating i) to j).

2. The method of claim 1:
   wherein determining the first growth stage is further based on a weather parameter associated with the first time; and
   wherein repeating b) to d) comprises determining a second growth stage for the plants based on an updated weather parameter using the first crop system, the updated weather parameter associated with the second time.

3. The method of claim 2:
   wherein determining the first nitrogen change is further based on a first nitrogen soil release determined based on the weather parameter using the nitrogen change system; and
   wherein e) comprises determining the second nitrogen change based on the second growth stage and a second nitrogen soil release determined based on the updated weather parameter using the nitrogen change system.

4. The method of claim 2, further comprising: receiving a third image of the geographic region, the third image associated with the second time, wherein determining the second growth stage is further based on the third image.

5. The method of claim 1, wherein determining the nitrogen prescription is based on predicted yield data and target yield data for the geographic region at a future time.

6. The method of claim 5, wherein the geographic region comprises a plurality of geographic sub-regions, wherein the predicted yield data comprises predicted yields for each geographic sub-region of the plurality, wherein the target yield data comprises target yields for each geographic sub-region of the plurality, and wherein determining the nitrogen prescription comprises determining sub-region nitrogen prescriptions for each geographic sub-region of the plurality based on differences between the predicted yields and the target yields.

7. The method of claim 1, wherein determining the first growth stage comprises:
    extracting a vegetative performance value for the geographic region from the first image;
    selecting a growth curve for the geographic region based on the vegetative performance value;
    determining a transition date based on the growth curve;
    selecting a growth phase model based on a current date and the transition date; and
    determining the first growth stage based on the growth phase model.

8. A method for managing nitrogen within a geographic region, the method comprising:
    a) receiving a first image of the geographic region from an imaging system, the first image corresponding to a first time;
    b) determining a growth stage at the first time for plants within the geographic region based on the first image using a crop system;
    c) determining a nitrogen change for the geographic region based on the growth stage using a nitrogen change system comprising:
        receiving sensor measurements sampled by the nitrogen application equipment, the sensor measurements sampled during a historic time;
        automatically determining an initial nitrogen amount for the geographic region at the historic time based on the sensor measurements; and
        determining the nitrogen change between the historic time to the first time based on the initial nitrogen amount;
    d) receiving a rainfall parameter for the geographic region, the rainfall parameter associated with the first time; and
    e) in response to the rainfall parameter exceeding a historic rainfall parameter, evaluating nitrogen status for the geographic region based on the rainfall parameter and a reflectance for the first image;
    f) in response to the nitrogen status indicating a nitrogen stress, determining a nitrogen prescription for the geographic region based on the nitrogen change using a nitrogen prescription system;
    g) generating first control instructions based on the nitrogen prescription, wherein nitrogen application equipment facilitates nitrogen application according to the first control instructions.

9. The method of claim 8, further comprising repeating b), c), f), and g) to generate second control instructions using the crop system with a second image corresponding to a second time.

10. The method of claim 8, further comprising:
    determining a predicted yield for the crops based on the nitrogen prescription;
    determining an actual yield for the geographic region; and
    calibrating a state specific factor of the nitrogen prescription system based on a difference between the predicted yield and the actual yield.

11. The method of claim 10, wherein determining the actual yield comprises:
    receiving harvest data from harvesting equipment; and
    automatically determining the actual yield from the harvest data.

12. The method of claim 10, wherein determining the actual yield comprises:
    receiving a second image of the geographic region, the second image corresponding to a second time within a time range preceding a scheduled harvest time;
    extracting a vegetative performance value from the second image; and
    determining the actual yield based on the vegetative performance value.

13. The method of claim 8, wherein determining the growth stage comprises:
    extracting a vegetative performance value for the geographic region from the first image; and
    determining the growth stage based on the vegetative performance value.

14. The method of claim 13, wherein determining the growth stage based on the vegetative performance value comprises:
    selecting a growth curve for the geographic region based on the vegetative performance value;
    determining a transition date based on the growth curve;
    selecting a growth phase model based on a current date and the transition date; and
    determining the growth stage based on the growth phase model.

15. The method of claim 8, wherein the geographic region comprises a plurality of geographic sub-regions, and wherein the growth stage and the nitrogen prescription are for a geographic sub-region of the plurality, the method further comprising:
    determining sub-region growth stages for remaining geographic sub-regions of the plurality based on the first image; and
    determining sub-region nitrogen prescriptions for the remaining geographic sub-regions based on the nitrogen change, wherein generating the first control instructions is further based on the sub-region nitrogen prescriptions.

* * * * *